United States Patent
Fong et al.

(10) Patent No.: US 9,910,032 B2
(45) Date of Patent: Mar. 6, 2018

(54) METHOD OF IDENTIFYING, ISOLATING AND/OR CULTURING FOETAL ERYTHROBLASTS

(75) Inventors: Chui Yee Fong, Singapore (SG); Ariffeen Bongso, Singapore (SG); Mahesh Choolani, Singapore (SG); Zhouwei Huang, Singapore (SG); Gauthaman Kalamegam, Singapore (SG); Sukumar Ponnusamy, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 14/111,159

(22) PCT Filed: Apr. 11, 2012

(86) PCT No.: PCT/SG2012/000130
§ 371 (c)(1),
(2), (4) Date: Oct. 10, 2013

(87) PCT Pub. No.: WO2012/141657
PCT Pub. Date: Oct. 18, 2012

(65) Prior Publication Data
US 2014/0030724 A1  Jan. 30, 2014

Related U.S. Application Data

(60) Provisional application No. 61/473,841, filed on Apr. 11, 2011.

(51) Int. Cl.
*G01N 33/50* (2006.01)
*C12N 5/0789* (2010.01)

(52) U.S. Cl.
CPC ....... *G01N 33/5094* (2013.01); *C12N 5/0647* (2013.01); *G01N 2800/00* (2013.01)

(58) Field of Classification Search
None
See application file for complete search history.

(56) References Cited

PUBLICATIONS

Migliaccio et al., Current Opinion in Hematology 2009, 16:259-268.*
Cha et al., "A simple and sensitive erythroblast scoring system to identify fetal cells in maternal blood," *Prenatal Diagnosis* 23:68-73, 2003.
Choolani et al, "Characterization of first trimester fetal erythroblasts for non-invasive prenatal diagnosis," *Molecular Human Reproduction* 9(4):227-235, 2003.
Traeger et al., "Approximately half of the erythroblasts in maternal blood are of fetal origin," *Molecular Human Reproduction* 5(12):1162-1165, 1999.

* cited by examiner

*Primary Examiner* — James D Schultz
(74) *Attorney, Agent, or Firm* — Seed IP Law Group LLP

(57) ABSTRACT

There is provided a method of identifying at least one foetal erythroblast in a sample, the method comprising analyzing the morphology of at least one cell in the sample; wherein at least one analyzed cell that is nucleated, is CD45 negative and comprises a relatively high cytoplasmic to nuclear ratio is identified as the foetal erythroblast.

10 Claims, 3 Drawing Sheets

METHOD OF IDENTIFYING, ISOLATING AND/OR CULTURING FOETAL ERYTHROBLASTS

FIELD OF THE INVENTION

The present invention relates to a method of identifying, isolating and/or culturing at least one foetal erythroblast. In particular, the invention relates to a method of identifying at least one foetal erythroblast in a sample by analysing the morphology of the foetal erythroblast, isolating the foetal erythroblast and/or culturing the foetal erythroblast in at least one optimised medium.

BACKGROUND TO THE INVENTION

Prenatal diagnosis provides valuable information on the health of the unborn child and can include invasive and non-invasive methods. The first reliable genetic diagnosis using amniocentesis was performed by Steele and Nerg in 1996. Later, first trimester chorionic villus sampling (CVS) was shown to be a safe and reliable approach for earlier prenatal diagnosis. Although both are invasive techniques and harbour potential risks of foetal miscarriage they are still considered to be the gold standards of prenatal diagnosis. Hence, these are slowly being replaced by the non-invasive prenatal diagnosis (NIPD) methods wherein foetal cells/genetic material obtained from maternal circulation are being utilized for prenatal diagnosis. In particular, identification of cell-free DNA, mRNA and foetal cells in the maternal circulation made the possibility of NIPD for diagnosis of chromosomal anomalies and single gene defects of the foetus. However, the foetal genetic materials obtained from the maternal circulation are rather insufficient to provide reliable information on chromosomal abnormalities. In particular, the cell-free DNA in maternal circulation is rather insufficient to provide complete chromosomal information such as aneuploidies for diagnosis and is also expensive. On the other hand, the foetal cells are promising candidates for detecting chromosomal abnormalities but their cell numbers are very few. In particular, the utilization of foetal cells circulating in the maternal blood is both promising for detection of aneuploidies as well as in providing complete genetic information of the foetus. Here again the major limitations are their scarcity in maternal circulation and lack of efficient separation techniques. Moreover, some of these cells might persist from previous pregnancy and may not be indicative of the current foetal status.

It is well known that prenatal diagnosis enables early identification of congenital birth defects and other risk factors that impair foetal survival, which in turn helps early intervention thereby avoiding complications and relieving parent anxiety. Of the various methods that are currently available, a diagnosis on isolated human primitive foetal erythroblasts (hPFEs) in the maternal circulation would be the most reliable and non-invasive strategy. This is because hPFEs have unique identification markers and their presence is definitely indicative of the current pregnancy and hence considered a potential candidate for early first trimester NIPD.

However, there are certain hurdles/problems that may be routinely encountered that need to be addressed to facilitate future-NIPD, and they are, (1) the numbers of circulating hPFEs in maternal circulation are very few and it is technically difficult to isolate these cells, (2) even upon successful isolation, these cells may not survive for long in the transport medium and may degenerate within a short period of time, thereby further limiting the possibility of screening for congenital defects and (3) hPFEs have very tightly condensed nuclei, and it is difficult to stimulate these cells to either prolong their life by in vitro culture or proliferate to get adequate cell numbers for future NIPD.

In view of the scarcity of foetal erythroblasts, to date no method has successfully identified and/or isolated foetal erythroblasts. Studies on foetal erythroblasts have relied only on heterogenous culture of cells, which may not provide accurate information in view of maternal cells or other impurities. Poor in vitro viability of foetal erythroblasts also severely limits the possibility of performing further analysis or studies on these cells.

Accordingly, there is a need in the art for a method for detecting, isolating and/or culturing foetal erythroblasts obtained by invasive or non-invasive means that alleviates at least one of the problems mentioned above and provides methods as potential reliable approaches for future NIPD using foetal cells present in maternal blood.

SUMMARY OF THE INVENTION

The present invention is defined in the appended independent claims. Some optional features of the present invention are defined in the appended dependent claims.

The present invention is directed towards a method of identifying foetal erythroblasts in a sample comprising determining the form and/or structure of at least one cell in the sample comprising at least one foetal erythroblast, wherein the cell which is being determined may be identified as a foetal erythroblast provided it comprises a nucleus, may be CD45 negative and/or may comprise relatively high cytoplasmic to nuclear ratio. The foetal erythroblast may be obtained by an invasive or non-invasive means.

According to one aspect, there is provided a method of identifying at least one foetal erythroblast in a sample, the method comprising analysing the morphology of at least one cell in the sample; wherein at least one analysed cell that is nucleated, is CD45 negative and comprises a relatively high cytoplasmic to nuclear ratio is identified as the foetal erythroblast.

According to another aspect, there is provided a method isolating at least one foetal erythroblast from a sample, the method comprising, identifying the foetal erythroblast according to any aspect of the present invention and isolating the foetal erythroblast using a means capable of isolating the foetal erythroblast individually.

According to yet another aspect there is provided a method of culturing at least one foetal erythroblast, the method comprising culturing the erythroblast in a medium comprising at least one mitogen and/or at least one epigenetic factor.

As will be apparent from the following description, specific embodiments of the present invention allow the identification, isolation and culture of foetal erythroblasts. The present invention also provides for a method of diagnosing at least one prenatal disorder in an individual, a medium for use in culturing the foetal erythroblasts, at least one isolated foetal erythroblast obtained using a method according to any aspect of the present invention and the like. This and other related advantages will be apparent to skilled persons from the description below.

BRIEF DESCRIPTION OF THE FIGURES

Specific embodiments of a test strip of the present invention will now be described by way of examples with reference to the accompanying figures in which.

DETAILED DESCRIPTION OF THE PREFERRED EMBODIMENTS

Figure 1:
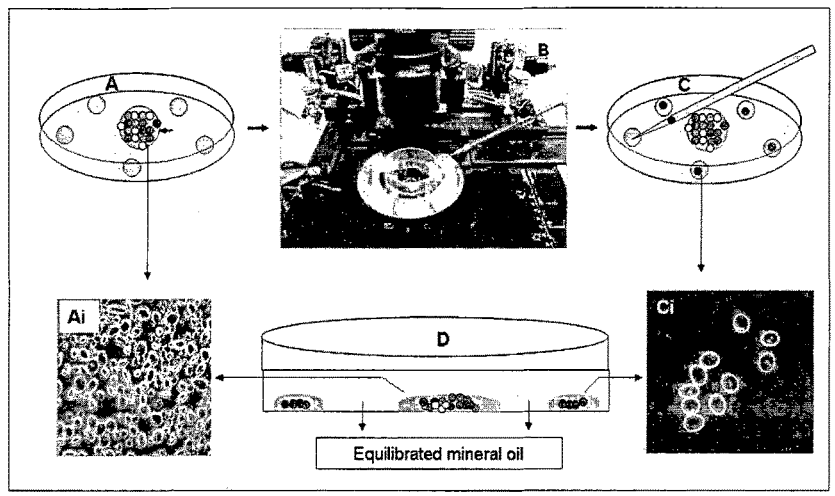
FIG. 1 is a schematic diagram of micromanipulation and microdroplet-culture of human primitive foetal erythroblasts (hPFEs).

Bibliographic references mentioned in the present specification are for convenience listed in the form of a list of references and added at the end of the examples. The whole content of such bibliographic references is herein incorporated by reference.

Reference to an element by the indefinite article "a" or "an" does not exclude the possibility that more than one of the element is present, unless the context clearly requires that there be one and only one of the elements. The indefinite article "a" or "an" as used herein thus usually means "at least one".

The term "comprising" and its conjugations is used in its non-limiting sense to mean that items following the word are included, but items not specifically mentioned are not excluded. Accordingly, the term "comprising" encompasses the more restrictive terms "consisting essentially of" and "consisting of."

The term "CD45 negative" as used herein refers to any cell that expresses no signal or is negative for native, recombinant or synthetic forms of the CD45 molecule/marker. The presence of CD45 expression on a cell in a sample may be determined using any immunostaining method known in the art and using any anti-CD45 reagent. Any cells positively stained with anti-CD45 reagent may be excluded as these may include CD45 positive white blood cells.

The phrase "cytoplasmic to nuclear ratio" (C/N; C:N ratio) may be used interchangeably with the phrase "ratio between cytoplasm and nucleus of a cell" or "cytoplasm to nucleus ratio" as used herein refers to a comparison of the area of cytoplasm and the area of nuclei present in the cytoplasm using any method known in the art. For example, a UV radiation reaction image may be used to obtain this measurement. The area of cytoplasm may or may not comprise cell well areas or internal cell structures like vacuoles, mitochondrial etc. The area of nuclei may or may not comprise nuclear membrane districts. In case more than one nucleus should be present in a cell, either the area of one nucleus may be determined or the area of all nuclei present may be determined. The ratio of cytoplasm and nucleus of a cell may be determined for each cell individually or for any grouping or sub-grouping of cells present in a defined area of the image, e.g. an area comprising about 100, 200, 300, 400, 500, 600, 700, 800, 900, 1000, 2000, 4000, 6000, 8000, 10000, 15000, 20000, 25000, 30000, 35000, 38000, 40000, 43000, 45000, 50000, 60000 or 70000 μm$^2$. In another example, the ratio of the region may be performed by calculating the surface area and/or volume of both cytoplasm and nucleus separately. A cell may be considered to have relatively high cytoplasmic to nuclear ratio as long as the area of cytoplasm is slightly more than the area of the nucleus in a cell. For example, as long as the cytoplasm is at least 0.1%, 0.5%, 1%, 5%, 10% larger than the nucleus, the cell may be considered to have a relatively high cytoplasmic to nuclear ratio. In specific examples, the term "high" refers to an area of cytoplasm that is detectably higher (increased) than the nucleus. In particular, the cytoplasmic to nuclear ratio may range from 20:1 to 5:1, 18:1 to 7:1, or 16:1 to 9:1, or any integers thereof. In particular, the C:N ratio of a foetal erythroblast may be 4:1, 6:1, 10:1 or the like.

The term "erythroblast" as used herein refers to a red blood cell having a nucleus. In particular, an erythroblast refers to a nucleated precursor cell from which a reticulocyte develops into an erythrocyte. "Erythroblast" may be used interchangeably with a "Normoblast" and refers to a nucleated red blood cell, the immediate precursor of an erythrocyte. For example, the erythroblast may be of mammalian origin. In particular, the erythroblast may be a primitive or human foetal erythroblast. "Erythrocytes" or "red blood cells" or "RBC" include non-nucleated adult and foetal red blood cells.

The term "globular" as used herein refers to a cell having a spherical shape (globelike shape) as opposed to a cell having biconcave shape.

The term "growth factor" as used herein refers to at least one protein that causes resting cells to undergo cell division and, in some cases, differentiation. Growth factors may either be cell type-specific, stimulating division of only those cells with appropriate receptors; or more general in their effects. Growth factors may include, but are not limited to, epidermal growth factor (EGF), nerve growth factor (NGF), fibroblast growth factor (FGF), platelet-derived growth factor (PDGF), erythropoietin, stem cell factor (SCF), granulocyte macrophage colony-stimulating factor (GM-CSF) and a family of proteins called lymphokines, which includes interleukins (IL-1, IL-2, IL-3, IL-6, etc.), interferon γ and the like.

The phrase "increasing the viability" as used herein refers to the act of increasing survival of a cell. This may include the increase in period of survival of the cell where it is still capable of maintaining its function. For example, the method of culturing as provided in the present invention may enhance or improve the survival of a cell to more than 24 hours in vitro. For example, the foetal erythroblast may be viable for at least 48 hours, 56 hours, 72 hrs, 1 week, 2 weeks and the like depending on the organism in question. For example, cell viability may be measured by cell counting i.e. count the number of viable cells and dead cells at each time point. Viable cells have clear and distinct plasma membrane under phase contrast microscopy, while non viable cells have disintegrated membranes making the nucleus more obvious.

The term "individually" as used herein refers to one cell at a time. For example, in the method of isolation of the present invention, each foetal erythroblast identified may be picked out one at a time for culturing the cell. A non-limiting example for a means to pick out a cell individually is a micromanipulator.

The term "malleability" as used herein refers to the capability of being extended or shaped by external influence. For example, cells that are malleable may be flexible, mouldable and/or pliable during aspiration into a micropipette. An isolated foetal erythroblast may be considered to be malleable.

The term "mammalian" is herein defined as a mammalian individual, in particular, a primate for example a human being. For purposes of research, the subject may be a non-human.

For example the subject may be an animal suitable for use in an animal model, e.g., a pig, horse, mouse, rat, cow, dog, cat, cattle, non-human primate (e.g. chimpanzee) and the like.

The term "microdroplet" as used herein refers to about 5 to about 20 μl of culture medium. In particular, the microdroplet may be 6, 7, 8, 10, 14, 15, 18 or 19 μl of culture medium.

The term "mitogen" as used herein refers to any chemical substance that promotes cell division and/or transformation. Non-limiting examples of mitogens may include concanavalin A, Phytohaemagglutinin, lipopolysaccharide (LPS), Insulin-like growth factors (IGFs), pokeweed mitogen, and the like.

The phrase "morphology of a cell" as used herein refers in general to the form, structure and configuration of a cell and may include aspects of the cell appearance like shape, colour or pattern of internal or external part of a cell. Morphology of a cell may also include nucleation of a cell, whether the cell is nucleated or not nucleated, whether the cell is CD45 negative or positive and/or the cytoplasm to nuclear ratio of the cell. Other aspects that may fall within the definition of morphology of a cell includes the size of the cell, for example the diameter of the cell, the adherence ability of the cell, for example whether the cell adheres or does not adhere to a surface, malleability of a cell and the like. The phrase "form of a cell" may be used interchangeably with the phrase "shape of a cell" and as used herein refers to typical cell forms like circular cells, elliptic cells, shmoo like cells, division forms like dumbbells, star-like cell forms, flat cells, scale-like cells, columnar cells, invaginated cells, cells with concavely formed walls, cells with convexly formed walls, the presence of prolongations, appendices or cilia, the presence of angles or corner etc. Typical morphologies or forms would be known to the person skilled in the art and can be derived from.

The term "nucleated" as used herein refers to a cell that has a nucleus. Nucleated cells may be distinguished from red blood cells which are not nucleated based on any nuclear staining known in the art.

The term "non adherence" as used herein refers to a cell that requires little to no support, anchor and/or attachment to a surface in order to remain viable in vitro.

The term "non-sticky cell surface" as used herein refers to a cell that does not adhere to each other unlike RBCs which tend to form "Rouleaux". A skilled person would understand the term "rouleaux formation" in relation to RBCs.

The phrase "normoxic condition" as used herein refers to an environment with normal oxygen level in vivo or in vitro. Normal oxygen state in vitro may be about at least 21% oxygen. The phrase "normoxic condition" is used as an antonym of "hypoxic condition" which refers to environment with reduced or depleted oxygen level in vivo or in vitro. Hypoxic oxygen state in vitro may be 5% oxygen.

The term "overlaid" as used herein in conjunction with the term "mineral oil" which refers to providing a layer of mineral oil over or upon culture medium.

The term "prenatal disorder" as used herein refers to diseases or conditions in a foetus or embryo before it is born. The prenatal disorder may be selected from the non-limiting group consisting of Down Syndrome, Edwards Syndrome, Patau Syndrome, a neural tube defect, spina bifida, cleft palate, Tay Sachs disease, sickle-cell anemia, thalassemia, cystic fibrosis, fragile X syndrome, spinal muscular atrophy, myotonic dystrophy, Huntington's disease, Charcot-Marie-Tooth disease, haemophilia, Duchenne Muscular Dystrophy, mitochondrial disorder, hereditary multiple exostoses, osteogenesis imperfecta disorder and the like.

The term "sample" as used herein refers to a subset of tissues, cells or component parts (for example fluids) that may include, but are not limited to, maternal tissue, maternal blood, cord blood, amniocenteses, chorionic villus sample, foetal blood, and/or foetal tissue/fluids. In particular, foetal tissue may be trophoblast tissue, placental tissue or a combination thereof. The sample as used in the present invention may have been previously subjected to a density gradient purification including, but not limited to, Ficoll gradient and Percoll gradient.

Invasive Prenatal Diagnosis/Invasive Prenatal Means

Amniocentesis

Chromosome analysis on aspirated amniotic fluid in the mid trimester of pregnancy (amniocentesis) was first carried out more than four decades ago (Kubli and Hindermann 1966). Today, it is the conventionally used method at 16-18 weeks of pregnancy causing low risk to the fetus after withdrawal of about 10-20 ml of fluid. Cells in the amniotic fluid are separated after the aspiration procedure and are grown in vitro in specially designed culture media to amplify cell numbers for later diagnosis. Approximately, 2 to $3 \times 10^5$ cells (Weise et al., 1984) can be harvested from 10 ml of amniotic fluid and the origins of these cells are from the inner lining of the amniotic membrane, skin, respiratory and urogenital tract of the fetus resulting from sloughing, urination and physical movements of the fetus within the amniotic sac. Amniocentesis has been routinely used for detecting chromosomal anomalies such as Down's, Edward's and Patau's syndromes, neural tube defects and other genetic disorders. Although amniocentesis is a routine tool for prenatal diagnosis in many hospitals, there are risks of miscarriage associated with its invasiveness. The rate of amniocentesis-related miscarriages has been reported to be about 1% (Tabor et al., 2009).

Chorionic Villus Sampling (CVS)

Chorionic villus sampling (CVS) as a tool for prenatal diagnosis was first developed in 1984 (Kuliev et al 1993). In this procedure, samples of chorionic villi are aspirated transcervically or transabdominally and the foetal cells within the tissue are used for diagnosis. The advantage of CVS over amniocentesis is that it can be performed at an earlier stage of pregnancy (usually before 14 weeks of gestation) providing early diagnosis and thus relieving much anxiety to the parents. CVS has been used for the detection of similar chromosomal anomalies as in amniocentesis. In the CVS method also there are risks of miscarriage in the region of about 2% (Tabor et al., 2009).

Foetal Blood Sampling

Foetal blood sampling, also known as percutaneous umbilical cord blood sampling is a procedure to remove a small amount of blood from the foetal umbilical cord. The foetal blood sample can be used for detecting chromosomal abnormalities, blood and metabolic disorders and infections and is useful when information cannot be obtained through amniocentesis and CVS. Foetal blood sampling is usually performed in late gestation after 17 weeks and has a high miscarriage rate of 2-3% (Buscaglia et al., 1996; Antsaklis et al., 1998).

Non-Invasive Prenatal Diagnosis (NIPD)/Non-Invasive Prenatal Means

Ultrasonography

Ultrasonography is a common non-invasive procedure done routinely for prenatal care. It helps visualizing the fetus in the uterus and provides information on its growth status. Important developmental abnormalities such as Down's syndrome can be detected using ultrasonography by evaluating the thickness of the nuchal fold and its translucency, and foetal organs. Although ultrasonography is very useful in monitoring foetal growth and detecting the phenotypes of developmental abnormalities, its false-positive rates are high. For example, in the nuchal translucency thickness test, about 5% of positive fetuses do not actually have Down's syndrome (Muller et al., 2003). Most foetal defects are caused by abnormal genetic make-up (chromosome number and morphology, gene defects) and as such many of them cannot be detected via ultrasound scan.

Maternal Serum Screening ("Triple Test")

Maternal serum screening, also called the 'triple test' is a blood test which helps determine the risk of certain chromosomal abnormalities such as Down's syndrome and neural tube defects. It is usually done in the first or second trimester of pregnancy by measuring a combination of serum levels of alpha-fetoprotein, estriol and human chorionic gonadotropin. A positive test indicates a high risk of the particular disorder but the diagnosis is not definitive. If the result is positive, then the diagnosis has to be further confirmed with other invasive procedures such as amniocentesis or CVS.

Preimplantation Genetic Diagnosis (PGD) in In Vitro Fertilization (IVF)

Preimplantation genetic diagnosis (PGD) is a special prenatal diagnosis test for patients going through In vitro Fertilization (IVF). In older IVF patients (>40 years) with potential aneuploidies due to age-related egg defects and those IVF patients with habitual miscarriages after embryo transfer due to possible imbalanced translocations, PGD on embryo biopsies has become a routine diagnostic tool. PGD is also available for many monogenic disorders such as cystic fibrosis and beta-thalassemia and some chromosomal abnormalities. The main advantage of this method is that it can avoid selective termination of pregnancy because only genetically normal embryos are transferred but its disadvantage is that it is reserved only for IVF patients.

Cell Free Foetal DNA and mRNA in Maternal Blood

Large amounts of cell-free foetal DNA circulating in maternal plasma and serum was first reported by Lo et al in 1997 and three years later cell-free foetal mRNA was also observed in the maternal plasma (Poon et al., 2000). Cell-free foetal DNA carries valuable genetic information of the fetus and was shown to be suitable for diagnosing foetal sex, foetal rhesus D (RhD) blood type, and some single-gene disorders such as beta-thalassemia and achondroplasia (ACH) (Saito et al., 2000; Chiu et al., 2002; Vrettou et al., 2003; Li, et al., 2005). However, because of the small amounts of cell-free foetal DNA in the total free DNA in the maternal plasma, the quantification of specific foetal loci from the cell-free foetal material is difficult and inefficient. This problem was overcome by the use of foetal mRNA which is specific to placental tissue minimising maternal background contamination. However, in using cell-free foetal DNA or mRNA, diagnosis of foetal aneuploidy remains the major difficulty for NIPD. Shotgun sequencing of cell-free foetal DNA was shown to give an accurate diagnosis of foetal aneuploidy (Fan et al., 2008). In a more recent study, the whole genetic profile of the fetus could be revealed by sequencing foetal cell free-DNA in the maternal blood (Lo et al., 2010). The same group conducted a larger scale study on maternal plasma samples using multiplexed DNA sequencing anaylsis and showed that it was able to rule foetal trisomy 21 among high risk pregnancies, thus avoiding invasive diagnostic procedures (Chiu. R W et al., 2011). However, before these newly developed techniques can be used for routine clinical application, trials on large sample numbers need be carried out to optimize the protocols and their cost effectiveness needs to be considered.

Foetal Cells in Maternal Blood

The presence of foetal cells in the maternal circulation was first documented by in 1893 when multinucleated syncytial trophoblasts were found in the lung tissue of pregnant women who died from eclampsia (Schmorl, 1893). This important observation laid the foundation for the use of foetal cells in maternal blood for non-invasive prenatal diagnosis. Intact foetal cells, compared to cell-free foetal DNA and mRNA, have the advantage of retaining complete foetal genetic information in the nucleus and cytoplasm that can provide information in complex genetic diagnosis. There are a variety of foetal cell types present in maternal blood, viz., trophoblasts, lymphocytes, erythroblasts and hematopoietic stem cells. Trophoblast cell trafficking does not occur commonly in pregnancy and their enrichment from the maternal blood is difficult due to lack of specific makers. Additionally, due to placental mosaicism, the karyotype of about 1% of placental cells is different from the actual karyotype of the fetus (Henderson et al., 1996; Goldberg and Wohlferd, 1997) leading to false positive and false negative genetic diagnosis. Therefore, the use of trophoblasts in maternal blood for NIPD is limited. Foetal lymphocytes present in maternal blood were previously shown to be useful for foetal sex determination (Walknowska et al., 1969; Schroer and De la Chapelle, 1972; Grosset et al., 1974) because of their ability to proliferate in vitro. However, their disadvantage is that it was shown that they could persist in maternal blood for a very long period of time even after 27 years postpartum (Bianchi et al., 1996) leading to misdiagnosis of the current pregnancy. Thus, a cell type with short lifespan is preferred and as such foetal erythroblasts (FEs) or nucleated red blood cells are good candidates for NIPD because they can be detected early in pregnancy, have short life spans, and specific antibodies can be developed for their enrichment from maternal blood. However, major challenges exist in the use of FEs because the number of FEs in maternal blood is small and estimated at 1 in $10^5$ to 1 in $10^9$ of mononuclear cells (Ganshirt-Ahlert et al., 1990; Price et al., 1991). On average approximately 20 FEs are obtained after enrichment of 20 ml of maternal blood (Busch et al., 1994). The final purity of FEs is low even when specific antibodies are used to sort them out from the maternal blood. Some workers have cultured foetal erythroid progenitors from the maternal blood which were proliferative with the hope that increased numbers of foetal cells could be obtained for prenatal diagnosis. However, because of the contamination of maternal cells in the culture, selective amplification of foetal over maternal progenitors was not successful in these studies (Lo et al., 1994; Bohmer et al., 2001; Campagnoli et al., 2002). Similar problems occurred when culturing CD34+ hematopoietic stem cells from maternal blood for prenatal diagnosis. Both the foetal and maternal CD34+ cells proliferated in culture, making it difficult to separate the two populations and perform a diagnosis on the foetal cells. CD34+ foetal stem cells have also found to persist post-delivery in maternal blood. Besides the problems of cell numbers and enrichment and in vitro expansion of foetal cells in maternal blood, the PCR analysis of these cells is often associated with a high level of allele drop-out as a result of the non-amplification of one of the two alleles. This would require the analysis of at least five to six foetal cells in order to offset the drop-out rate (Hahn et al., 2008).

Methods of enrichment of FEs from maternal blood include fluorescence-activated cell sorting (FACS), magnetic activated cell sorting (MACS), density gradient centrifugation, charged flow separation, selective erythrocyte lysis and lectin-based methods. FACS and MACS are based on antigen-antibody recognition using specific antibodies for the target foetal cells. The first monoclonal antibody used to enrich foetal erythroblast was CD71 (Bianchi et al., 1990) but the purity of FEs after sorting remained low. Purity was later improved by using MACS depletion of anti-CD45 prior to positive selection of CD71 positive cells (Busch et al., 1994). To assess the potential of FEs for NIPD, a large-scale multicentric study was carried out, known as NIFTY, between 1995 and 1999 (Bianchi et al., 2002). Results from this study showed that MACS separation yielded better recovery of FEs compared to FACS separation. However, in both methods, FEs were difficult to detect, most likely due to the scarce number of these cells in maternal blood. This study concluded that the separation method based on interactions between the cell-specific antigen and the corresponding antibodies has its limitations. To remove mature erythrocytes from maternal blood, selective density gradient systems were developed to enrich mononuclear cells. Various density gradients using Percoll and Ficoll were tried on separating FEs from the rest of the cells in the maternal blood but the recovery rates were still very low (Troeger et al, 1999; Samura et al., 2000; Prieto et al., 2001; Voullaire et al., 2001). The ideal enrichment protocol for FEs from maternal blood with high recovery rates and purity still needs to be developed.

Primitive Foetal Erythroblasts

Two distinct types of erythropoiesis have been reported during mammalian embryo development (1) primitive erythropoiesis in the yolk sac and (2) definitive erythropoiesis mainly in the foetal liver and bone marrow. While definitive erythropoiesis is well studied in the adult, primitive erythropoiesis is less understood due to its transient presence in the early fetus. It was recognized very early that primitive erythroid cells emerged in the yolk sac blood islands (Maximow et al., 1909) and primitive erythropoiesis was the first developmental process producing erythrocytes to supply oxygen for the survival and growth of the fetus. One study showed that human primitive erythroblasts were the only circulating red cells present within the fetus and its yolk sac until week 6 (Pereda and Niimi, 2008). Some studies have indicated however that primitive erythropoiesis arises from haemangioblast precursors in the mesoderm layer of the yolk sac wall (Ema et al., 2006; Choi et al., 1998; Lugus et al., 2009).

Primitive red cells, also called primitive erythroblasts are distinguishable from definitive red blood cells in that they start circulating in the blood stream as nucleated cells and contain an embryonic type of haemoglobin viz., epsilon-globin. The dogma existed for a long time that primitive erythroblasts share many features with their non-mammalian counterparts such as being nucleated throughout the whole life-span. Whether primitive erythroblasts enucleate has been a puzzle ever since they were discovered and extensively studied in murine models in recent years. In the mouse fetus, there was evidence showing that primitive erythroblasts undergo enucleation in the foetal liver (Kingsley et al., 2004; Fraser et al., 2007). After erythroblast enucleation there were two populations of cells generated, namely reticulocytes and pyrenocytes which are excluded nuclei surrounded by a thin rim of cytoplasm. Pyrenocytes are rapidly removed by macrophages by phagocytosis (Yoshida et al., 2005; McGrath et al., 2008). In the human, due to ethical sensitivities and practical reasons, not many studies have been done on primitive erythropoiesis. Van Handel et al (2010) recently suggested that the human placenta was the anatomical site for primitive erythroblast enucleation and that enucleation probably required interaction with macrophages in the chorionic villi.

Stemness Properties of pFEs

In the adult bone marrow, hematopoietic stem cells (HSC) are able to self-renew and differentiate into all the blood lineages. When the specific differentiation pathway is decided for HSCs towards an erythroid lineage, the downstream progenitor cells are also capable of self-renewal, but in a more restricted way as they continue to further differentiate. In adult definitive erythropoiesis, immature erythroid-restricted progenitors called erythroid burst-forming units (BFU-E) have a better proliferative ability than late-stage erythroid progenitors [erythroid colony-forming units (CFU-E)]. CFU-E subsequently differentiate into a cascade of erythroid precursors which undergo three to four cell divisions as they progress from proerythroblast to basophilic, polychromatophilic and orthochromatic erythroblast stages. Orthochromatic erythroblasts finally enucleate to produce reticulocytes which enter the blood stream and soon become erythrocytes. Interestingly, a type of definitive erythroid precursor cell derived from early mouse embryos (yolk sac and foetal liver) was recently found to have extensive proliferation potential ex vivo, much better than their adult counterparts (England et al., 2010). In the same study, erythroid precursors from primitive erythropoiesis were also cultured but found not to be proliferative.

Although primitive erythropoiesis was suggested to originate from the haemangioblast, the maturation process of primitive erythroid cells is similar to that of definitive erythropoiesis as shown in the murine model (Palis et al., 2010). Human primitive erythropoiesis is not well studied but may share many common features with the mouse model. Nevertheless, it is not clear yet whether human primitive erythroblasts undergo the same differentiation process as mouse primitive erythroblasts which eventually enucleate to form reticulocytes. The self-renewal potential of human primitive erythroblasts has also not been explored probably due to ethical concerns and difficulty of accessing such cells. Given the fact that morphologically, pFEs have varied nuclear and cytoplasmic sizes like like human embryonic stem cells (hESCs) and the fact that they are blast cells, it would be important to investigate whether they possess stemness properties. It thus may be useful to investigate the presence of stemness-related surface marker antigens and CD marker profiles on the human primitive erythroblasts. There is a whole battery of characteristic markers for identifying stem cells with long term self-renewal property. Since primitive erythroblasts originate from the mesoderm of the early embryonic yolk sac membrane, markers of human embryonic stem cells (hESC), mesenchymal stem cells and hematopoietic stem cells should be evaluated on this cell type. Human embryonic stem cells (hESCs) have typical surface marker antigens such as SSEA3, SSEA4, Tra-1-60 and Tra-1-81 and nuclear antigens such as OCT4, SOX2 and NANOG. Hematopoietic stem cells are positive for CD34, CD45 and CD117 while mesenchymal stem cells markers vary from one cell type to another but generally they are positive for CD73, CD90, CD105, and negative for CD45, CD34 and CD14. In terms of transcription profile, hESCs have high expressions of OCT4, SOX2, NANOG, LIN28, c-MYC and KLF4, all of which help maintain self-renewal capacity and pluripotency. Increased alkaline phosphatase and telomerase levels are also two markers indicative of stemness in embryonic cells. After checking all these stemness markers on human primitive erythroblasts it may be possible to identify which differentiation stage it belongs to in the primitive hematopoiesis process and whether it is a progenitor cell that can self-renew and differentiate further or whether it is already a terminally differentiated cell.

Morphology of the Primitive Foetal Erythroblast (pFE)

The human primitive erythroblast has a high cytoplasmic-nuclear ratio and is a larger size compared to definitive erythroblasts and it shares some common properties with definitive erythroblasts. Interestingly, high nuclear-cytoplasmic ratio is a feature of human embryonic stem cells (Bongso et al 1994). Primitive erythroblasts undergo morphological changes consistent with definitive erythroblast maturation. As primitive erythroblasts mature, increasing amounts of haemoglobin are accumulated in their cytoplasm (De la Chapelle et al., 1969), they become smaller in size (Henery et al., 1992), their nuclei condense progressively (Sasaki et al., 1985) and they lose intermediate filaments with the nucleus being free to move about in the cytoplasm (Sangiorgi et al., 1990). One distinct feature of primitive erythroblasts is that they circulate in the blood in a nucleated state unlike definitive erythroblasts which enucleate before they enter the circulation. Primitive erythroblasts isolated from the maternal blood of pregnant women have slightly different morphology compared to those in the fetus. They usually possess pyknotic nuclei which are very condensed. This may be caused by the difference in oxygen concentration between the maternal and foetal blood (Babochkina et al., 2005).

pFE for NIPD

Despite the limitations of using foetal cells in maternal blood for NIPD, studies on their enrichment, culture and PCR efficiency still continue. The first trimester primitive FE (pFE) is still considered a promising candidate for early NIPD because it appears early in gestation within the first trimester, has a short half-life and can be distinguished from maternal nucleated erythrocytes using unique embryonic haemoglobin markers (Choolani et al., 2003). However, like other foetal cells, pFEs are very rare in the maternal blood. The cell number problem still poses difficulties of using them for a reliable prenatal diagnosis even if they can be enriched with specific markers. What's more, in the human, this type of erythroblast has not been extensively studied probably due to its transient presence in the fetus and limited accessibility. In the following sections, recent information on the nature and properties of pFEs will be described and some novel approaches will be discussed on how this foetal cell type may be manipulated to increase cell numbers for NIPD.

Accordingly, according to one aspect, there is provided a method of identifying at least one foetal cell in a sample, the method comprising analysing the morphology of at least one cell in the sample; wherein at least one analysed cell that is nucleated, is CD45 negative and comprises a relatively high cytoplasmic to nuclear ratio is identified as the foetal cell. In particular, the foetal cell may be a foetal erythroblast cell. More in particular, the foetal erythroblast may be a mammalian foetal erythroblast. Even more in particular, the foetal erythroblast may be a primitive or human foetal erythroblast.

Advantageously, these characteristics may provide for simple yet accurate identification of foetal cell in a sample. Further, the method of identifying the foetal erythroblast according to any aspect of the present invention may provide solutions that include:
- a method of selecting, picking and isolating each individual hPFE;
- a clean and pure in vitro culture environment to observe, culture and study the enucleation process of isolated hPFE from maternal blood;
- helping to extend the maintenance and/or viability of hPFEs in vitro isolated from maternal blood; and/or
- improving/enhancing the detection of genes which may otherwise be difficult to detect due to the closed/condensed nature of the hPFEs.

In particular, foetal erythroblast may have a high cytoplasmic to nuclear ratio (by area) ranging from 20:1 to 5:1, 18:1 to 7:1, or 19:1 to 10:1, or any integers thereof. Foetal erythroblast may have relatively high cytoplasmic to nuclear ratio in view of their highly condensed nuclei and large cytoplasm. More particularly, the foetal erythroblast may have high cytoplasmic to nuclear ratio ranging from 16:1 to 9:1. The characteristic of having relatively high cytoplasmic to nuclear ratio (by area) advantageously allows for specific and easy identification of foetal erythroblast without the need to resort to specific cell staining. This advantageously reduces the amount of time and/or costs required for preparing the sample before isolation. Without limiting the scope of the present invention, it is believed that the characteristic of high cytoplasmic to nuclear ratio is due to the highly condensed nuclei and large cytoplasm nature of foetal erythroblast.

The identified foetal erythroblast may be further identified as having an average diameter within a range of 10-20 µm, 12-18 µm, or 14-17 µm. More particularly, the foetal erythroblast may have an average diameter of 15-16 µm.

Other features that may be used to identify foetal erythroblast include the non adherence and/or globular nature of these foetal erythroblasts. Foetal erythroblast has a smooth non-sticking cell surface and may be malleable during cell aspiration into the micropipette. Foetal erythroblast may also be more globular in shape as compared to red blood cells which are biconcave. These characteristics enable the foetal erythroblast to be easily aspirated and expelled using instruments such as pipettes without damaging the erythroblast.

According to another aspect, there is provided a method of isolating at least one foetal cell from a sample, the method comprising, identifying the foetal cell according to the method as described in the present invention and isolating the foetal cell using a means capable of isolating the foetal cell individually.

There are many protocols available for enriching foetal erythroblasts from maternal blood samples, such as fluorescent-activated cell sorting, magnetic-activated cell sorting, density gradient centrifugation, lectin-based methods and the like. However, the recovery and purity of the target cells from these protocols may be considered to be generally low. Pure foetal erythroblasts used for prenatal diagnostic tests are important for accurate results. In order to address this problem, this method of isolation utilizes micromanipulation technique for isolating individual hPFEs from maternal blood.

In particular, the isolation of the mammalian nucleated foetal cell from the sample may be performed using, but not limited to, a micromanipulator or any system that allows individual picking of a foetal cell. In particular, the foetal cell may be a mammalian foetal erythroblast. More in particular, the foetal cell may be a primitive or human foetal erythroblast.

The micromanipulation concept m adopted from In vitro Fertilization programs in which 2 micropipettes are used; one to hold the oocyte in the right position and the other to pick up a single spermatozoon under the microscope to be injected into the oocyte. The micromanipulation method used here requires only one micropipette which may be customized with an internal diameter of between 20-25 µm to suit the target cell size and a flat tip end to prevent physical damage on the cells.

According to a further aspect there is provided an isolated foetal erythroblast obtained according to any method of the present invention.

Micromanipulation and Microdroplet Culture of Primitive Foetal Erythroblasts (pFEs)

Besides separation methods using density gradients and flow sorting to enhance enrichment and purity of FEs from maternal blood, the micromanipulation methods used in IVF programs to pick-up single spermatozoon with micropipettes under the microscope for intracytoplasmic injection into an oocyte (ICSI) would be a novel method of separating pFEs from maternal cells. An efficient system using a Zeiss-Narashige micromanipulation system was developed and 20 µm bore micropipettes to pick up individual pFEs. Additionally, 10 µl microdroplets of culture medium under sterile equilibrated mineral oil (Sigma Chemical Co, MO) was used to house and observe single pFE enucleation and monitor their cell behaviour and growth in vitro. The microdroplets of culture medium contained pure populations of pFEs (FIG. 1). Their growth behaviour and number can be accurately tracked over time because there is no contamination of other cell types which are commonly present in the blood. With this microdroplet culture system, the effects of different gas environments, medium composition, mitogens and growth factors on pFEs can be studied so as to develop the optimal culture environment for the expansion of pFEs.

Density gradients and flow sorting methods have been employed to enhance enrichment and purity of FEs from maternal blood. However, these methods would still contain a mixture of few other cell types. In contrast, the micromanipulation method that is conventionally used in In vitro Fertilization (IVF) programs to pick-up single spermatozoon with micropipettes under the microscope for intracytoplasmic injection into an oocyte (ICSI) would be a novel method of separating hPFEs from maternal cells. An efficient and clean system using a Zeiss-Narashige micromanipulation system was developed and 20 µm bore micropipettes to select, pick, and isolate individual hPFEs. Additionally, 10 µl microdroplets of culture medium under sterile equilibrated mineral oil (Sigma Chemical Co, MO) was used to house and observe single hPFE enucleation and monitor their cell behaviour and growth in vitro. The microdroplets of culture medium contained pure populations of hPFEs. The combination of both methods namely, micromanipulation, to manually select, pick and isolate hPFEs and subsequent micro-droplet culture enables (1) study of the enucleation process and growth behavior, and (2) track a fixed number of cells accurately over time and possibly prolong their viability in vitro. This strategy would offer a very clean system of homogenous hPFEs culture for use in future NIPD.

Manipulating pFE for NIPD

Ex Vivo Culture of pFEs

For many years the ex vivo expansion in culture of foetal cells from maternal blood has been attempted by many groups to provide adequate cell numbers for reliable NIPD (Table 1). Foetal erythroid precursor cells, hematopoietic stem cells, mesenchymal stem cells and endothelial precursor cells were used for such expansion culture because they had the potential to proliferate ex vivo. However, two major challenges exist in such culture expansion, (1) the enrichment of the few target foetal cells from the large number of maternal blood cells and (2) developing the optimal culture system that will favour the growth of foetal cells over maternal cells. When the sex of the cultured cells was examined using fluorescent in situ hybridization (FISH), PCR and foetal haemoglobin staining techniques, most of the expanded cells turned out to be of maternal origin despite the various culture systems used (Chen et al., 1998; Han et al., 1999; Bohmer et al., 2002). This was most likely due to the scarcity of foetal cells in the maternal blood. A specific marker for distinguishing the foetal cells from maternal cells is therefore critical in the enrichment step. An optimal combination of cytokines allowing foetal over maternal cell growth needs to be developed.

TABLE 1

Ex vivo culture of foetal cells from maternal blood for non-invasive prenatal diagnosis (NIPD).

| Year | Authors | Cell type | Gestation in weeks | No. of samples | Assays |
|---|---|---|---|---|---|
| 1994 | Lo et al. | Erythroid cells | 11-20 | 5 | FISH |
| 1996 | Valerio et al. | BFU-E, CFU-E | 14-16 | 8 | PCR, FISH, HbF |
| 1997 | Little et al. | CD34+ cells | 10-13 | 42 | FISH |
| 1997 | Valerio et al. | BFU-E, CFU-E, CFU-GEMM | 17-22 | 7* | FISH |
| 1998 | Chen et al. | BFU-E, CFU-E | 9-17 | 16 | PCR, FISH, HbF |
| 1999 | Han et al. | CD71/GPA+ cells | 10 | 1 | PCR, HbF |
| 1999 | Bohmer et al. | Nucleated red cells | 18 | 1 | FISH |
| 2000 | Jansen et al. | CD34+ cells | 7-16 | 65 | FISH |
| 2000 | Valerio et al. | Erythroid cells | 19 | 1* | FISH |
| 2000 | Huber et al. | Erythroid cells | 12, 17 | 26 | PCR, FISH, HPLC |
| 2000 | Tutschek et al. | BFU-E, CFU-GM | 14-20 | 14 | PCR |
| 2001 | Coata et al. | CD34+ cells | 11-16 | 31 | PCR, FISH |
| 2001 | Han et al. | Erythroid cells | 8-14 | 10 | PCR, HbF |

TABLE 1-continued

Ex vivo culture of foetal cells from maternal blood
for non-invasive prenatal diagnosis (NIPD).

| Year | Authors | Cell type | Gestation in weeks | No. of samples | Assays |
|---|---|---|---|---|---|
| 2002 | Campagnoli et al. | CD34+ cells | 10-40 | 49 | FISH |
| 2002 | Zimmermann et al. | Erythroid cells | 13-41 | 16 | PCR |
| 2002 | Manotaya et al. | CD34+ cells | 5-21 | 17 | PCR, FISH |
| 2002 | Gussin etal. | Endothelial precursor cells | 13-26 | 13 | FISH |
| 2002 | Bohmer et al. | Nucleated red cells | 11-25 | 25 | PCR, FISH |
| 2003 | Donoghue et al. | Fetal MSC | 7-13 | 20 | FISH |

*indicates Trisomy

Thus far no study has been done on the ex vivo culture of first trimester human primitive erythroblasts from maternal blood. The reasons for this may be that human primitive erythroblasts are more predominant in early gestation (Choolani et al., 2001; 2003), and the knowledge generated for this cell type is limited. How the human primitive erythroblast behaves ex vivo is not known but from what is already known in murine primitive erythropoiesis, the primitive erythroblast at an early differentiation stage is able to proliferate for a few cycles in order to give rise to more mature daughter cells (Palis et al., 2010). Thus, the cell cycle profile of primitive erythroblasts at different weeks of gestation and the percentage of cells at various mitotic phases that can be analysed need to be studied. With such information, it is possible to know at what gestational age primitive erythroblasts have more proliferation potential for ex vivo culture for NIPD.

According to another aspect, there is provided a method of culturing at least one foetal cell, the method comprising culturing the cell in a medium comprising at least one mitogen and/or at least one epigenetic factor. The culture medium of the present invention surprisingly improves the viability of foetal cell in vitro. Without at least one mitogen and/or at least one epigenetic factor, foetal cell may not be cultured in vitro for extended period of time (i.e. more than one day). Thus, the medium may be capable of increasing the viability of the foetal cell.

In particular, the foetal cell may be foetal erythroblast. More in particular, the foetal cell may be mammalian foetal erythroblast. Even more in particular, the foetal cell may be human foetal erythroblast.

Mitogens

Mitogens are chemical substances that encourage a cell to commence cell division. Usually they trigger signalling pathways such as the mitogen-activated protein kinase (MAPK) pathway which leads to mitosis. Concanavalin A, Phytohaemagglutinin and pokeweed mitogen are common mitogens routinely used to stimulate lymphocyte proliferation in clinical laboratory medicine. Upon exposure to these mitogens, lymphocytes are activated and able to divide again and produce immune responses. Since pFEs are also of a blood lineage like lymphocytes it would be interesting to examine the effects of these mitogens on FEs to stimulate mitosis and increase cell numbers for NIPD. Some signalling pathways may be triggered and as a result these mitogens may improve the proliferative potential of the human pFE.

Mitogens are chemical substances that promote cell division. Mitogen-activated protein kinase (MAPK) pathways and cell cycle regulatory pathways are influenced by these mitogens which lead to mitosis. Some of the common mitogens used to stimulate lymphocyte proliferation are Concanavalin A, Phytohaemagglutinin and pokeweed mitogen. It would be interesting to examine the effects of these mitogens on hPFEs to stimulate mitosis and increase cell numbers for NIPD. Activation of MAPK and other cell cycle regulatory pathways by these mitogens may improve the proliferative potential of the hPFE. Pokeweed mitogen could extend the viability of FEs significantly in vitro.

In particular, mitogens that may be used in the culture medium according to any aspect of the present invention includes, but is not limited to concanavalin A, phytohaemagglutinin, lipopolysaccharide (LPS), Insulin-like growth factors (IGFs), pokeweed mitogen and/or the like.

Epigenetic Factors/Small Molecules in Ex Vivo Culture, Maintenance and Expansion of hPFEs The ex vivo expansion in culture of foetal cells from maternal blood has been attempted by many groups to provide adequate cell numbers for reliable NIPD (Lo et al., 1994; Valerio et al., 1996; Chen et al., 1998; Jansen et al., 2000; Han et al., 2001; Zimmerman et al., 2002; Donoghue et al., 2003). Of the various foetal cell types the human primitive erythroblast (hPFEs) is a potential candidate cell for first trimester NIPD as these cells have unique markers of identification (eglobulin) (Choolani et al., 2001; 2003). Enucleation is a natural phenomenon in the maturation of murine foetal erythroblasts. However, current knowledge on human primitive erythroblast maturation, enucleation and other properties are limited. However, the retention of nucleus within the cytoplasm becomes indispensable before a genetic diagnosis can be performed by NIPD. Therefore ways of delaying the enucleation process may be needed if enucleation does occur also in humans. Recent studies on mouse definitive erythroblasts showed that histone deacetylation induced by histone deacetylase (HDAC) played an important role in definitive erythroblast nuclear condensation and enucleation (Popova et al., 2009; Ji et al., 2010). When HDAC inhibitors such as trichostatin A was added to mouse definitive erythroblasts, nuclear condensation and enucleation were inhibited. Whether or not the HDAC inhibitors delay the enucleation of hPFEs need to be evaluated. HDAC inhibitors may decondense the nucleus of the hPFE. It is possible that this might play an important role, such as to either delay or prevent enucleation and hence prolonging their viability in vitro and therefore enabling prenatal diagnosis even after a delayed period of at least 48 to 72 hours.

The primitive erythroblast is a good target cell for first trimester NIPD. Most of the knowledge on the nature and properties of primitive erythroblasts is gained from murine models and it is therefore difficult to make conclusions on human primitive erythroblast maturation, enucleation and other properties. If human primitive erythroblasts do enucleate in vivo, it may be worth studying this phenomenon in vitro for the application of NIPD. The nucleus should be retained within the cytoplasm before a genetic diagnosis can be performed and therefore ways of delaying the enucleation process may be needed if enucleation does occur in vitro. Recent studies on mouse definitive erythroblasts showed that histone deacetylation induced by histone deacetylase (HDAC) played an important role in definitive erythroblast nuclear condensation and enucleation (Popova et al., 2009; Ji et al., 2010). When HDAC inhibitors such as trichostatin A was added to mouse definitive erythroblasts, nuclear condensation and enucleation were inhibited. Therefore one might ask will HDAC inhibitors delay the enucleation of primitive erythroblasts as well. HDAC inhibitors may decondense the nucleus of the human primitive erythroblast and may play an important role in enucleation. However, the mechanisms behind primitive erythroblast enucleation may be different from that of the definitive erythroblast.

Epigenetic factors that may be included in the culture medium includes, but are not limited to at least one agent that promotes decondensation of a nucleus and/or at least one agent that delays enucleation. The agent that promotes decondensation of a nucleus may be a histone deaceylase inhibitor that may include, but is not limited to, Tricostatin A (TSA), Suberoylanilide hydroxamic acid (SAHA) or vorinostat, Belinostat, Panobinostat, Oxamflatin, Depsipeptides, Trapoxins, Depudecin, MS-27-275, Valproic acid, Butyric acid and Apicidin.

The agent that delays enucleation is DNA methyl transferase inhibitor that may include, but not limited to, 5-azacytidine, 5-aza-2-deoxycytidine, 1-R-D-arabinofuranosyl-5azacytosine, Dihydro-5-azacytidine, Zebularine, Procaine, Epigallocatechin-3-gallate (EGCG), RG108, L-ethionine, Procainamide hydrochloride, Psammaplins, Hydralazine hydrochloride, Oligonucleotide MG98 and the like.

In particular, the method of culturing the foetal cell may be carried out under normoxic conditions. More particularly, the foetal cell may be cultured in normoxic conditions with oxygen level of about 18%-about 22%, about 19%-about 21% or about 20%-about 21.5%.

In particular, the method of culturing the foetal cell according to the present invention maintains the foetal cell in a medium that is capable of increasing the viability of the foetal erythroblast. More particularly, the medium may be capable of maintaining the cell viability of the foetal erythroblast for at least 48 hours, 72 hours, 1 week, 2 weeks and the like.

In particular, the method of culturing the foetal cell according to the present invention may maintain the foetal cell in a microdroplet. More particularly, the microdroplet may be overlaid with at least one oil. The presence of the oil may prevent evaporation and rapid cooling of culture medium containing the foetal cell.

Oil that may be used in the method of culturing may include, but is not limited to, mineral oil, silicon oil, vegetable oil and the like. In particular, the oil used according to any aspect of the present invention may be at least one mineral oil. The term "mineral oil" refers to any colourless, odourless, light mixtures of alkanes in the C15 to C40 range from a non-vegetable source. Mineral oil as used herein is equilibrated mineral oil that may be obtained when mineral oil is mixed with culture medium and incubated until all nutrients from the culture medium have diffused to the mineral oil, thus reaching equilibrium in nutrient content between mineral oil and culture medium.

The method according to any aspect of the present invention may include methods to isolate and expand these hPFEs for use in future NIPD. These include (1) the use of micromanipulation methods for individually selecting, picking, and isolating the hPFEs, (2) the use of the microdroplet culture method to purify and study hPFEs from maternal blood as a homogenous cell population, (3) the use of mitogens to increase hPFE numbers and (4) the use of epigenetic factors/small molecules to decondense the nucleus and activate gene transcription to facilitate hPFE proliferation. All the above novel strategies would enable successful NIPD. Once the hPFEs are picked and isolated, they may be sent for genetic testing if the number is sufficient or be expanded using in vitro microdroplet-culture system as shown in FIG. 1. Most groups have cultured foetal erythroid progenitors from the maternal blood in large volume of medium in a Petri dish expecting that the foetal cell number can be increased for diagnosis, but due to the contamination of maternal cells in the culture, selective amplification of foetal over maternal cells was not successful.

According to another aspect, there is provided a method of promoting and/or facilitating proliferation of at least one foetal cell ex vivo, the method comprising contacting at least one mitogen to the foetal cell. In particular, the mitogen may be selected from the group consisting of concanavalin A, phytohaemagglutinin, lipopolysaccharide (LPS), Insulin-like growth factors (IGFs) and pokeweed. The foetal cell that may be used in the method according to the present invention may be human primitive foetal erythroblasts.

In particular, the foetal cell may be foetal erythroblast. More in particular, the foetal cell may be mammalian foetal erythroblast. Even more in particular, the foetal cell may be human foetal erythroblast.

According to another aspect, there is provided a medium for culturing at least one foetal cell, the medium comprising at least one mitogen and/or at least one epigenetic factor and/or the medium is free from at least one growth factor. In particular, the medium may be capable of increasing the viability of the foetal erythroblast. More in particular, the medium may be capable of maintaining the cell viability of the foetal erythroblast for at least 48 hours.

In particular, the culture medium may comprise mitogen that may be selected from the group consisting of concanavalin A, phytohaemagglutinin, lipopolysaccharide (LPS), Insulin-like growth factors (IGFs) and pokeweed. More in particular, the culture medium may further comprise an agent that delays enucleation and/or promotes decondensation of a nucleus.

Nuclear Reprogramming of pFEs

Viral and Non-Viral Reprogramming

A recent breakthrough in the field of stem cell biology has been the generation of induced pluripotent stem cells (iPSC) from somatic cells by ectopic expression of a battery of four genes viz., KLF4, OCT4, SOX2 and c-MYC (KOSM factors) (Takahashi et al., 2007). It is now clear that differentiated somatic cells can be reverted back to the embryonic state by using nuclear reprogramming techniques including somatic cell nuclear transfer (SCNT), cell fusion, cell-free extracts and the iPSC approach. In nuclear reprogramming, the cell DNA content will not be lost during cell differentiation, but the transcription status of all the genes change dynamically and constantly by epigenetic modifications in order to suit the functional role the cell plays at a particular developmental stage and in a particular location in the body. After the report of Takahashi et al (2006), another group later showed that by using LIN28 instead of KLF4 in the KOSM factors the same iPSCs could be generated from somatic cells (Yu et al., 2007). These six genes used for production of iPSCs play essential roles in maintaining the pluripotency and indefinite self-renewal potential in embryonic stem cells. In the differentiated cells, these genes may have been shut down or expressed at very low levels to avoid unnecessary cell potencies. By introducing these active genes back into the cell, they will be transcribed and translated to active transcription factors that act on the cell genome and activate certain gene expressions, thus changing the transcription profile of the cell and reverting it back to an embryonic state. Initially, retroviral and lentiviral vectors carrying the reprogramming factors were used to generate iPSCs because of their higher gene delivery efficiency compared to non-viral transfection methods. However, viral integration in the host cell genome may lead to insertional mutagenesis which poses a big concern for clinical application. Soon after the success of producing iPSC from several types of somatic cells, non-viral approaches were rapidly developed to avoid the use of viruses for iPSC generation. In the recently devised piggyback transposon/transposase system, transgenes flanked by piggyBac terminal repeats were inserted into the host genome and removed after the pluripotency was established (Woltjen et al., 2009). Here, there was no residual genomic integration in the host cell and thus the host cell genome was not changed but activated to the embryonic state. Transient repeated transfection of cells with only plasmids has also resulted in iPSC generation although the efficiency was extremely low (Okita et al., 2010). Other than transgene-based methods, direct delivery of proteins (Kim et al., 2009; Zhou et al., 2009) and messenger RNA encoding the transcription factors (Yakobov et al., 2010) were also able to generate iPSCs.

Use of Small Molecules for Reprogramming

Interestingly, many small molecules have been shown to be able to enhance the efficiency of iPSC generation significantly (Li and Ding, 2009). For example, using the small molecules SB431542 and PD0325901 to inhibit TGF and MAPK/ERK pathways, human fibroblasts could be reprogrammed with the KOSM factors with 200-fold enhanced efficiency (Lin et al., 2009). Some of the small molecules can even replace one or more of the reprogramming factors. For example, human fibroblasts were reprogrammed to iPSCs with only OCT4, SOX2 and addition of valproic acid (VPA) (Huangfu et al., 2008). Valproic acid, a HDAC inhibitor, can increase histone acetylation thus activating the transcription of certain genes whose promoters were previously repressed due to histone deacetylation. In a recent study, neonatal human keratinocytes were reprogrammed to iPSCs with only Oct4 and a cocktail of chemical compounds that modulate epigenetic status, cellular metabolism and signalling pathways (Zhu et al., 2010). Interestingly, this study indicated that a metabolic switch to anaerobic glycolysis which is mainly used by pluripotent cells is important for reprogramming somatic cells to the pluripotent state. Small molecules that modulate different aspects of cellular activities may eventually lead to the goal of reprogramming cells with only chemical molecules without transgenes.

Efficiency of Reprogramming

Besides safety issues, reprogramming efficiency of iPSC technology is another big concern when considering its clinical applications. Viral-mediated reprogramming methods have higher efficiency than non-viral methods, but yet it can only reach up to 1% efficiency with the help of small molecules. Non-viral approaches are more ideal but overall have very low efficiency ranging from 0.001% to 0.01% (Kiskinis and Eggan, 2010). The efficiency of reprogramming also depends on the target cell type. Less differentiated cells such as progenitor cells and stem cells can be reprogrammed at a much higher efficiency compared to terminally differentiated cell types such as adult skin fibroblasts and lymphocytes from peripheral blood. This is probably due to the fact that in a fully differentiated cell, more features that are required for differentiation need to be changed before the cell can go back to a non-differentiated state. Based on current knowledge, iPSC reprogramming itself is a stochastic process, but amenable to acceleration (Hanna et al., 2009). The use of small molecules may greatly enhance reprogramming efficiency by pre-setting the target cells to a more reprogrammable status which allows the immediate effects of the reprogramming factors on the cells.

Cell Reprogramming for Non-Invasive Prenatal Diagnosis (NIPD)

Figure 2:
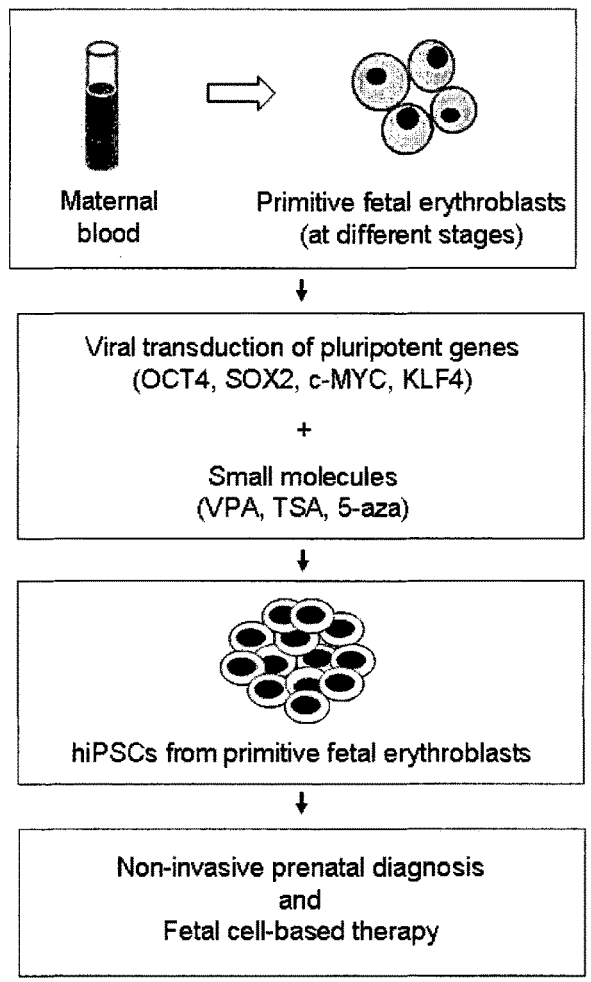
FIG. 2 is a schematic representation of human induced pluripotent stem cells (hiPSCs) that may be generated from primitive foetal erythroblasts (pFEs) using pluripotent genes and small molecules. VPA: Valproic acid; TSA: trichostatin A; 5-aza: 5-azacytidine.

As iPSC technology advances, safer reprogramming strategies targeting a broader range of cell types with higher efficiencies will be developed in the near future. It will be beneficial in the field of foetal medicine if the iPSC technique can be applied to foetal cells. Foetal cells from amniotic fluid and chorionic villi have been reprogrammed to iPSCs successfully (Ye et al., 2009) which in turn can be differentiated into desirable tissues for intra-uterine foetal therapy. Additionally, foetal cells may have a higher reprogramming efficiency to iPSCs or require a lesser number of reprogramming factors than adult cells due to minimal somatic mutations and higher endogenous expression levels of the reprogramming factors. iPSC generation from human blood has gained much interest recently because blood is readily available and the collection procedure is not so invasive. iPSCs have been successfully generated from hematopoietic stem cells, T lymphocytes and myeloid cells (Staerk et al., 2010) but not from erythroid cells (Table 2). In the setting of NIPD using foetal cells from maternal blood, if the small number of enriched foetal cells could be reprogrammed to iPSCs (FIG. 2), cell numbers would no longer be a problem for performing a reliable diagnosis as the ensuing iPSCs will be proliferative and at the same time can be differentiated for cell based therapies. Since the pFE is a good target cell for NIPD, it may be useful to apply various iPSC methods on it to see whether it could be reprogrammed and its numbers could be amplified via the generation of actively dividing hESC-like colonies. There would be technical challenges in producing iPSCs from small numbers of pFEs given the overall low reprogramming efficiency. As reprogramming technology becomes more and more efficient, refined and established, manipulating foetal cells in the maternal blood for both NIPD and foetal cell-based therapy may become a reality in the future.

TABLE 2

Generation of induced pluripotent stem cells (iPSCs) from blood cells using viral reprogramming methods.

| Cell Type | Reprogramming factors | Method of delivery | Efficiency | Reference |
|---|---|---|---|---|
| CD34+ cells from mobilized human peripheral blood | Oct4, Sox2, c-Myc, Klf4 | Retroviral vectors | 0.01%-0.02% | Loh YH et al., 2009 |
| Human cord blood - derived endothelial cells | Oct4, Sox2, Nanog, Lin28 | Lentiviral vectors | 0.01%-0.03% | Haase A et al., 2009 |
| Human cord blood - derived CD133+ cells | Oct4, Sox2, c-Myc, Klf4 | Retroviral vectors | 0.002%-0.007% | Glorgetti A, et al., 2009 |
| Mouse mature B lymphocytes | Oct4, Sox2, c-Myc, Klf4, c/EBP$^\alpha$ | Doxycycline-inducible lentiviral vectors | 0.01%-0.1% | Hanna J et al., 2008 |
| Human T lymphocytes from peripheral blood | Oct4, Sox2, c-Myc, Klf4 | Doxycycline-inducible polycistronic lentiviral vectors | 0.0002%-0.001% | Staerk J et al., 2010 |

According to another aspect, there is provided a method of diagnosing at least one prenatal disorder in an individual, the method comprising: identifying at least one foetal cell in a sample of the individual, isolating the foetal cell, culturing the foetal cell, determining at least one genetic marker associated with the prenatal disorder in the foetal cell.

The foetal cell may be foetal erythroblast. The foetal erythroblast may be human or non-human. In particular, the foetal cell may be a mammalian foetal erythroblast. More in particular, the foetal cell may be a human foetal erythroblast.

The prenatal disorder that is selected from the group consisting of Down Syndrome, Edwards Syndrome, Patau Syndrome, a neural tube defect, spina bifida, cleft palate, Tay Sachs disease, sickle-cell anemia, thalassemia, cystic fibrosis, fragile X syndrome, spinal muscular atrophy, myotonic dystrophy, Huntington's disease, Charcot-Marie-Tooth disease, haemophilia, Duchenne Muscular Dystrophy, mitochondrial disorder, hereditary multiple exostoses and osteogenesis imperfecta disorder.

The sample may be selected from the group consisting of maternal tissue, maternal blood, cord blood, amniocytes, chorionic villus sample, foetal blood, foetal tissue and the like.

The method of diagnosing according to any aspect of the present invention may be the in vivo or in vitro.

A person skilled in the art will appreciate that the present invention may be practised without undue experimentation according to the method given herein. The methods, techniques and chemicals are as described in the references given or from protocols in standard biotechnology and molecular biology text books.

EXAMPLES

Standard molecular biology techniques known in the art and not specifically described were generally followed as described in Sambrook and Russel, Molecular Cloning: A Laboratory Manual, Cold Springs Harbor Laboratory, New York (2001).

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Method of Selecting, Picking and Isolating Each Individual hPFE

During the cell picking process, a few criteria were followed to help identify the hPFEs from the mass population of adult RBCs and other nucleated cell types. These criteria were developed based on studies done on hPFEs isolated from placental tissues at gestations of 8-10 weeks. They were: 1) hPFEs have an average diameter of 15-16 μm, which is about twice of diameter of RBCs; 2) hPFEs are nucleated cells, so they can be distinguished from RBCs based on nuclear staining; 3) hPFEs are CD45 negative. A one step immunostaining with anti-CD45 FITC can be used to exclude CD45 positive white blood cells which constitute most of the contaminating nucleated cells; 4) hPFEs are non-adherent cells with smooth non-sticking cell surface; 5) are quite malleable during cell aspiration into the micropipette; 6) hPFEs have a high cytoplasmic-to-nuclear ratio (by area) ranging from 16:1 to 9:1, due to their highly condensed nuclei and large cytoplasm; and 7) hPFEs are generally more globular shape as compared to RBCs which are biconcave.

Based on the above criteria, the cells were identified as hPFEs and were separated by the micromanipulation-microdroplet culture methodology as described in FIG. 1, which describes micromanipulation-microdroplet culture methodology for isolation of primitive foetal erythroblasts (pFEs) from a chorionic villus sample. In brief, A: Heterogeneous population of cells in a CVS were provided lying in the centre large droplet (arrow) which was previously subjected to separation with a Percoll gradient. Ai: Magnified phase contrast image of the heterogeneous cell population before micromanipulation. B, C: pFEs from the CVS in the large centre droplet were individually picked up using a 20 μm bore micropipette and Zeiss-Narashige micromanipulator under the microscope and transferred to 10 μl microculture droplets under sterile mineral oil in the periphery to obtain homogenous populations of pFEs. Ci: Magnified phase contrast images of pFEs in the peripheral microculture droplets that can be individually monitored. D: Cross-sectional view showing the microculture droplets of medium in a large Petri dish (60 mm) covered by a thin layer of equilibrated mineral oil.

In Vitro Culture Environment

A clean and pure in vitro culture environment was used to observe, culture and study the enucleation process of isolated hPFE from maternal blood. After the hPFEs were isolated from maternal blood, hPFEs could be sent for genetic testing if the number was sufficient or be expanded using in vitro microdroplet-culture system (FIG. 1). The microdroplet-culture system was adapted from the In vitro Fertilization programmes where oocytes and embryos were cultured in small milieu of culture medium. This microdroplet-culture system allowed in vitro culture of a pure population of hPFEs in a droplet of 10 µl medium covered with equilibrated mineral oil to prevent evaporation. More significantly, it allowed in vitro observation, tracking and study of the biological behaviour of each hPFE, such as cell enucleation by staining and tracking the nucleus. This was possible as each hPFE was cultured singly in each droplet of culture medium. The medium used for the cell culture was home-made with a composition of IMDM (Iscove's modified Dulbecco's medium)+30% FBS (foetal bovine serum)+ 1% BSA (bovine serum albumin)+$10^{-4}$ mol/l β-mercaptoethanol+100 µg/ml iron-saturated transferrin+1% AA (antibiotic antimycotic).

The microdroplet-culture system was used to maintain the viability of hPFEs in vitro by optimizing their culture conditions. Cell viability was measured by cell counting i.e. counting the number of viable cells and dead cells at each time point. Viable cells had clear and distinct plasma membrane under phase contrast microscopy, while non viable cells had disintegrated membranes making the nucleus more obvious.

Figure 3:
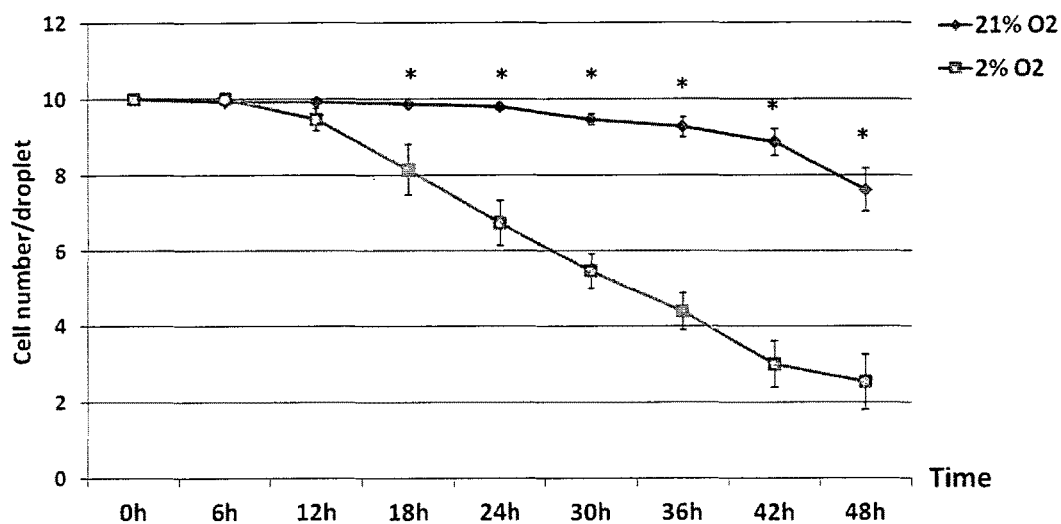
FIG. 3 is a graph of the viability of hPFEs cells under normoxic and hypoxic microdroplet-culture over time. Error bar represents standard errors. * $p<0.01$.
Figure 4:
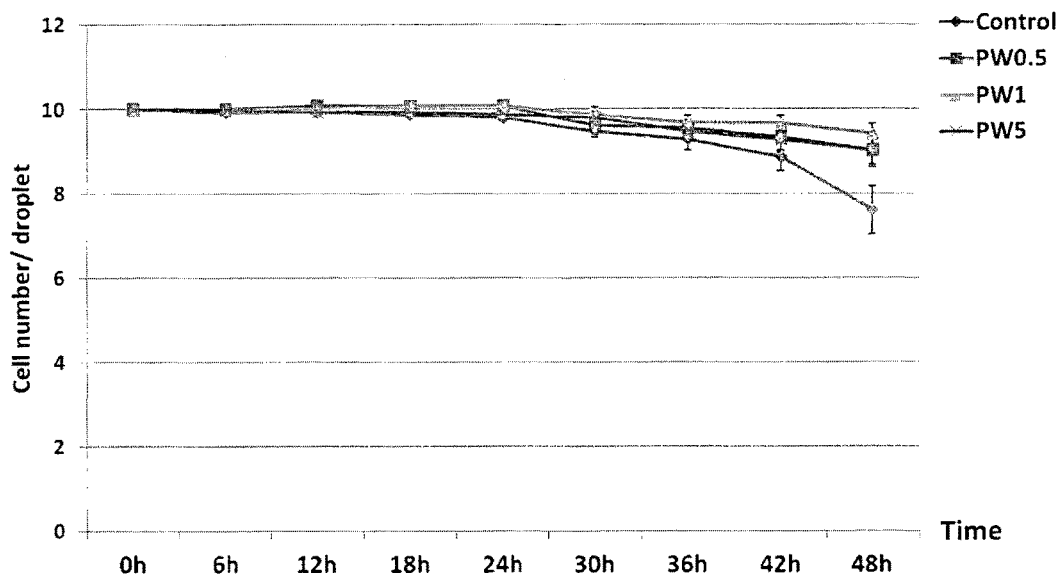
FIG. 4 is a graph of the viability of hPFEs under normoxic microdroplet-culture condition with Pokeweed mitogen up to 48 hours. Error bar represents standard errors. Pokeweed (PW) concentration unit is μg/ml.
Figure 5:
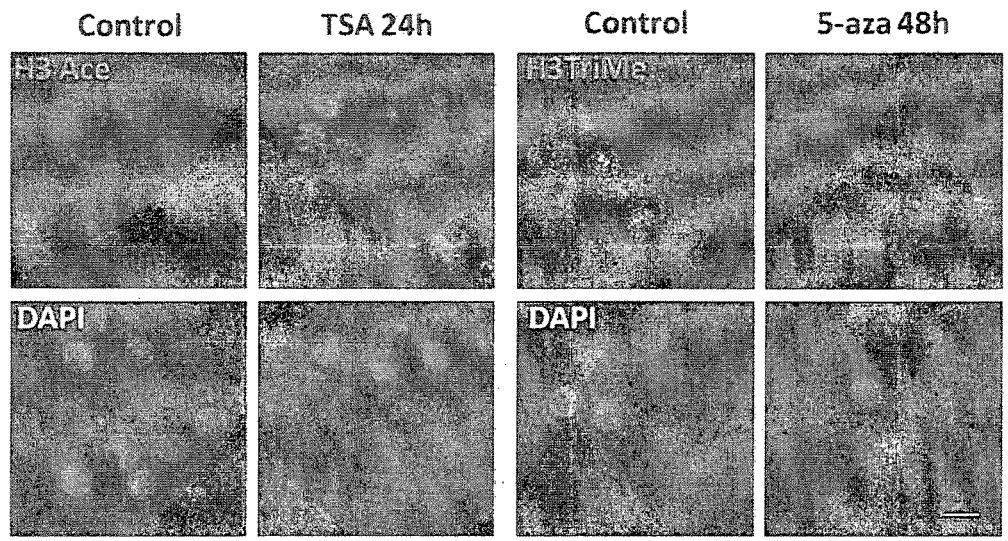
FIG. 5 are images of immunocytochemistry of hPFEs with anti-acetylated H3 and anti-trimethylated H3 antibodies. Scale bar is 5 μm.
Figure 6:
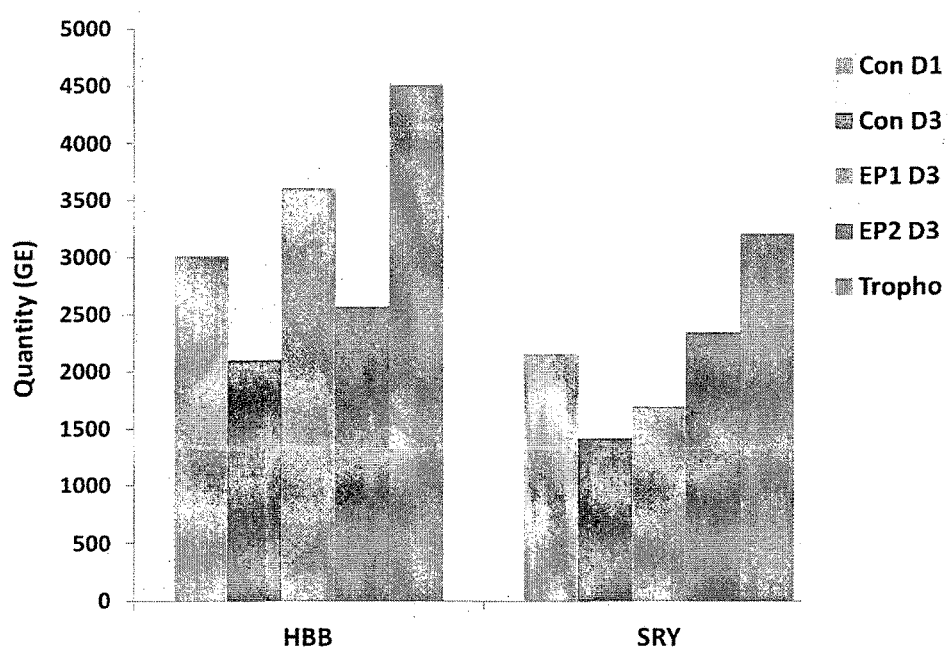
FIG. 6 is a bar graph of the human beta-globin (HBB) and Sex-determining region Y (SRY) expressions as detected by quantitative PCR on 10 hPFEs after whole genome amplification. EP1=Trichostatin A, EP2=5-azacytidine. Trophoblast DNA was used as a positive control.

The culture conditions were optimized for the hPFEs isolated from placental tissues, and it was found that hPFEs survived better under normoxic than hypoxic gaseous environment (FIG. 3). In addition, Pokeweed mitogen helped to maintain the viability of hpFEs for an extended period of time in culture, had a protective effect on the hPFEs, and decreased cell death as shown in FIG. 4. The use of the microdroplet-culture system thus extended the maintenance and viability of hPFEs in vitro isolated from maternal blood Decondensation of Nucleus The detection of genes which may otherwise be difficult to detect due to the closed/condensed nature of the hPFEs was made possible my decondensation of the nucleus of the isolated hPFEs. The nucleus of hPFE is normally highly condensed and has always caused difficulty in detecting the specific genes for prenatal diagnosis. A histone deacetylase inhibitor and a DNA methyl transferase inhibitor were used to decondense or remodel the chromatin structure of hPFEs. After treating the cells with these epigenetic factors, the histone acetylation level was increased and histone trimethylation level was reduced, which resulted in less condensed chromatin structure (FIG. 5). To evaluate the effects of epigenetic factors on gene detection, the genome of treated and non-treated hPFEs were amplified and the copy number of human beta-globin (HBB) and Sex-determining region Y (SRY) were measured with quantitative PCR. Results showed that on average, compared to the non-treated hPFEs, those treated with histone deacetylase inhibitor had higher copy number of HBB, and those treated with DNA methyl transferase inhibitor had higher copy number of SRY (FIG. 6).

REFERENCES

1. Sambrook and Russel, Molecular Cloning: A Laboratory Manual, Cold Springs Harbor Laboratory, New York (2001).
2. Antsaklis A, Daskalakis G, Papantoniou N, Michalas S. 1998. Foetal blood sampling-indication-related losses. Prenat Diagn. 18: 934-940.
3. Babochkina T, Mergenthaler S, Napoli G De, Hristoskova S, Tercanli S, Holzgreve W, Hahn S. 2005. Numerous erythroblasts in maternal blood are impervious to fluorescent in situ hybridization analysis, a feature related to a dense compact nucleus with apoptotic character. Hematologica 90: 740-745.
4. Bianchi D W, Flint A F, Pizzimenti M F, Knoll J H, Latt S M. 1990. Isolation of foetal DNA from nucleated erythrocytes in maternal blood. Proc Natl Acad Sci USA 87: 3279-3283.
5. Bianchi D W, Zickwolf G K, Weil G J, Sylvester S, De Maria M A. 1996. Male foetal progenitor cells persist in maternal blood for as long as 27 years postpartum. Proc Natl Acad Sci USA 93: 705-708.
6. Bianchi D W, Simpson J L, Jackson L G, Elias S, Holzgreve W, Evans M I, Dukes K A, Sullivan L M, Klinger K W, Bischoff F Z, Hahn S, Johnson K L, Lewis D, Wapner R J, de la Cruz F. 2002. Foetal gender and aneuploidy detection using foetal cells in maternal blood: analysis of NIFTY I data. National Institute of Child Health and Development Foetal Cell Isolation Study. Prenat Diagn 22: 609-615.
7. Bohmer R M, Zhen D K, Bianchi D W. 1999. Identification of foetal nucleated red cells in co-cultues from foetal and adult peripheral blood: differential effects of serum on foetal and adult erythropoiesis. Prenat Diagn 19: 628-636.
8. Bohmer R M, Johnson K L, Bianchi D W. 2001. Foetal and maternal progenitor cells in co-culture respond equally to erythropoietin. Prenat Diagn 21: 818-823.
9. Bohmer R M, Stroh H P, Johnson K L, LeShane E S, Bianchi D W. 2002. Foetal cell isolation from maternal blood cultures by flow cytometric hemoglobin profiles. Foetal Diagn Ther 17: 83-89.
10. Bongso A, Fong C Y, Ng S C, Ratnam S S. 1994. Isolation and culture of inner cell mass cells from human blastocysts. Hum Reprod. 9: 2110-2117.
11. Buscaglia M, Ghisoni L, Bellotti M, Ferrazzi E, Levi-Seth P, Marconi A M, Taglioretti A, Zamperini P, Pardi G. 1996. Percutaneous umbilical blood sampling: indication changes and procedure loss rate in a nine years' experience. Foetal Diagn Ther. 11: 106-113.
12. Busch J, Huber P, Holtz J, Pfluger E, Radbruch A. 1994. Simple and fast 'double-MACS' sorting of foetal erythroblasts from maternal blood for PCR-based paternity analysis. Ann NY Acad Sci 731: 144-146.
13. Campagnoli C, Roberts I A, Kumar S, Choolani M, Bennett P R, Letsky E, Fisk N M. 2002. Expandability of haemopoietic progenitors in first trimester foetal and maternal blood: implications for non-invasive prenatal diagnosis. Prenat Diagn 22: 463-469.
14. Chen H, Griffin D K, Jestice K, Hackett G, Cooper J, Ferguson-smith M A. 1998. Evaluating the culture of foetal erythroblasts from maternal blood for non-invasive prenatal diagnosis. Prenat Diagn 18: 883-892.
15. Chiu R W, Lau T K, Leung T N, Chow K C, Chui D H, Lo Y M. 2002. Prenatal exclusion of beta thalassaemia major by examination of maternal plasma. Lancet 360: 998-1000.
16. Chiu R W, Akolekar R, Zheng Y W, Leung T Y, Sun H, Chan K C, Lun F M, Go A T, Lau E T, To W W, Leung W C, Tang R Y, Au-Yeung S K, Lam H, Kung Y Y, Zhang X, van Vugt J M, Minekawa R, Tang M H, Wang J, Oudejans C B, Lau T K, Nicolaides K H, Lo Y M. 2011. Non-invasive prenatal assessment of trisomy 21 by multiplexed maternal plasma DNA sequencing: large scale validity study. BMJ doi: 10.1136/bmj.c7401.

17. Choi K, Kennedy M, Kazarov A, Papadimitriou J C, Keller G. 1998. A common precursor for hematopoietic and endothelial cells. Development 125:725-732.
18. Choolani M, O'Donnell H, Campagnoli C, Kumar S, Roberts I, Bennett P R, Fisk N M. 2001. Simultaneous foetal cell identification and diagnosis by epsilon-globin chain immunophenotyping and chromosomal fluorescence in situ hybridization. Blood 94: 554-557.
19. Choolani M, O'Donoghue K, Talbert D, Kumar S, Roberts I, Letsky E, Bennett P R, Fisk N M. 2003. Characerization of first trimester foetal erythroblasts for non-invasive prenatal diagnosis. Mol Human Reprod 9: 227-235.
20. Coata G, Tilesi F, Fizzotti M, Lauro V, Pennacchi L, Tabilio A, Di Renzo G C. 2001. Prenatal diagnosis of genetic abnormalities using foetal CD34+ stem cells in maternal circulation and evidence they do not affect diagnosis in later pregnancies. Stem Cells 19: 534-542.
21. De la Chapelle A, Fantoni A, Marks P. 1969. Differentiation of mammalian somatic cells: DNA and hemoglobin synthesis in foetal mouse yolk sac erythroid cells. Proc Natl Acad Sci USA 63: 812-819.
22. De la Chapelle A, Fantoni A, Marks P A. 1969. Differentiation of mammalian somatic cells: DNA and haemoglobin synthesis in foetal mouse yolk sac erythroid cells. Proc Natl Acad Sci USA 63: 812-819.
23. Donoghue K O, Choolani M, Chan J, Fuente J, Kumar S, Campagnoli C, Bennett P R, Roberts I A G, Fisk N M. 2003. Identification of foetal mesenchymal stem cells in maternal blood: implications for non-invasive prenatal diagnosis. Mol Hum Reprod 9: 497-502.
24. Ema M, Yokomizo T, Wakamatsu A, Terunuma T, Yamamoto M, Takahashi S. 2006. Primitive erythropoiesis from mesodermal precursors expressing VE-cadherin, PECAM-1, Tie2, endoglin, and CD34 in the mouse embryo. Blood 108: 4018-4024.
25. England S J, McGrath K E, Frame J M, Palis J. 2010. Immature erythroblasts with extensive ex vivo self-renewal capacity emerge from the early mammalian fetus. Blood. doi:10.1182/blood-2010-07-299743
26. Fan H C, Blumenfeld Y J, Chitkara U, Hudgins L, Quake S R. 2008. Noninvasive diagnosis of foetal aneuploidy by shotgun sequencing DNA from maternal blood. Proc Natl Acad Sci USA 105: 16266-16271.
27. Fraser S T, Isern J, Baron M H. 2007. Maturation and enucleation of primitive erythroblasts during mouse embryogenesis is accompanied by changes in cell surface antigen expression. Blood 109: 343-352.
28. Ganshirt-Ahlert D, Pohlschmidt M, Gal A, Miny P, Horst J, Holzgreve W. 1990. Ratio of foetal to maternal DNA is less than 1 in 5000 at different gestational ages in maternal blood. Clin Genet 38: 38-43.
29. Giorgetti A, Montserrat N, Aasen T, Gonzalez F, Rodríguez-Pizà I, Vassena R, Raya A, Boués, Barrero M J, Corbella B A, Torrabadella M, Veiga A, Izpisua Belmonte J C. 2009. Generation of induced pluripotent stem cells from human cord blood using OCT4 and SOX2. Cell Stem Cell 5: 353-357.
30. Goldberg J D, Wohlferd M M. 1997. Incidence and outcome of chromosomal mosaicism found at the time of chorionic villus sampling. Am J Obstet Gynecol 176: 1349-1352.
31. Grosset L, Barrelet V, Odartchenko N. 1974. Antenatal foetal sex determination from maternal blood during early pregnancy. Am J Obstet Gynecol 120: 60-63.
32. Gussin H A, Bischoff F Z, Hoffman R, Elias S. 2002. Endothelial precursor cells in the peripheral blood of pregnant women. J Soc Gynecol Investig 9: 357-361.
33. Haase A, Olmer R, Schwanke K, Wunderlich S, Merkert S, Hess C, Zweigerdt R, Gruh I, Meyer J, Wagner S, Maier L S, Han D W, Glage S, Miller K, Fischer P, Schöler H R, Martin U. 2009. Generation of induced pluripotent stem cells from human cord blood. Cell Stem Cell 5: 434-441.
34. Han J Y, Je G H, Kim I H, Rodgers G P. 1999. Culture of foetal erythroid cells from maternal blood using a two-phase liquid system. Am J Med Genet 87: 84-85.
35. Han J Y, Lee Y H, Sin S D, Park J I, Kim I H, Je G H, Rodgers G P. 2001. Enrichment and detection of foetal erythroid cells from maternal peripheral blood using liquid culture. Prenat Diagn 21: 22-26.
36. Hanna J, Markoulaki S, Schorderet P, Carey B W, Beard C, Wernig M, Creyghton M P, Steine E J, Cassady J P, Foreman R, Lengner C J, Dausman J A, Jaenisch R. 2008. Direct reprogramming of terminally differentiated mature B lymphocytes to pluripotency. Cell 133: 250-264.
37. Hanna J, Saha K, Pando B, van Zon J, Lengner C J, Creyghton M P, van Oudenaarden A, Jaenisch R. 2009. Direct cell reprogramming is a stochastic process amenable to acceleration. Nature 462: 595-601.
38. Hahn S, Zhong X Y, Holzgreve W. 2008. Recent progress in non-invasive prenatal diagnosis. Semin Foetal Neonatal Med 13: 57-62.
39. Henderson K G, Shaw T E, Barrett I J, Telenius A H, Wilson R D, Kalousek D K. 1996. Distribution of mosaicism in human placentae. Hum Genet 97: 650-654.
40. Henery C C, Kaufman M H. 1992. Relationship between cell size and nuclear volume in nucleated red blood cells of developmentally matched diploid and tetraploid mouse embryos. J Exp Zool. 261:472-478.
41. Huangfu D, Osafune K, Maehr R, Guo W, Eijkelenboom A, Chen S, Muhlestein W, Melton D A. 2008. Induction of pluripotent stem cells from primary human fibroblasts with only Oct4 and Sox2. Nature 26: 1269-1275.
42. Huber K, Bittner J, Worofka B, Rosen A, Hafner E, Philipp K, Bauer K. 2000. Quantitative FISH analysis and in vitro suspension cultures of erythroid cells from maternal peripheral blood for the isolation of foetal cells. Prenat Diagn 20: 479-486.
43. Jansen M W, Korver-Hakkennes K, van Leenen D, Brandenburg H, Wildschut, H I, Wladimiroff J W, Ploemacher R E. 2000. How useful is the in vitro expansion of foetal CD34+ progenitor cells from maternal blood samples for diagnostic purposes? Prenat Diagn 20: 725-731.
44. Ji P, Yeh V, Ramirez T, Murata-Hori M, Lodish H F. 2010. HDAC2 is required for chromatin condensation and subsequent enucleation of cultured mouse foetal erythroblasts. Haematologica 95: 2013-2021.
45. Kim D, Kim C H, Moon J I, Chung Y G, Chang M Y, Han B S, Ko S, Yang E, Cha K Y, Lanza R, Kim K S. 2009. Generation of human induced pluripotent stem cells by direct delivery of reprogramming proteins. Cell stem cell 4: 472-476.
46. Kingsley P D, Malik J, Fantauzzo K A, Palis J. 2004. Yolk sac-derived primitive erythroblasts enucleate during mammalian embryogenesis. Blood 104: 19-25.
47. Kiskinis E, Eggan K. 2010. Progress toward the clinical application of patient-specific pluripotent stem cells. J. Clin. Invest. 120: 51-59.

48. Kubli F, Hindermann P. 1966. Transabdominal amniocentesis and feto-maternal microtransfusion. Geburtsshife Frauenheilkd 26: 1244-1255.
49. Kuliev A M, Modell B, Jackson L, Simpson J L, Brambati B, Rhoads G, Froster U, Verlinsky Y, Smidt-Jensen S, Holzgreve W., Ginsberg N, Ammala P, Dumez Y. 1993. Risk evaluation of CVS. Prenat Diagn 13: 197-209.
50. Li Y, Di Naro E, Vitucci A, Zimmermann B, Holzgreve W, Hahn S. 2005. Detection of paternally inherited foetal point mutations for beta-thalassemia using size-fractionated cell-free DNA in maternal plasma. JAMA 293: 843-849.
51. Li W, Ding S. 2010. Small molecules that modulate embryonic stem cell fate and somatic cell reprogramming. Trends Pharmacol Sci 31: 36-45.
52. Lin T, Ambasudhan R, Yuan X, Li W, Hilcove S, Abujarour R, Lin X, Hahm H S, Hao E, Hayek A, Ding S. 2009. A chemical platform for improved induction of human iPSCs. Nat Methods 6: 805-808.
53. Little A T, Langlois S, Wilson D, Lansdorp P M. 1997. Frequency of foetal cells in sorted subpopulations of nucleated erythroid and CD34+ hematopoietic progenitor cells from maternal peripheral blood. Blood 89: 2347-2358.
54. Lo Y M, Morey A L, Wainscoat J S, Fleming K A. 1994. Culture of foetal erythroid cells from maternal peripheral blood. Lancet 344: 264-265.
55. Lo Y M, Corbetta N, Chamberlain P F, Rai V, Sargent I L, Redman C W, Wainscoat J S. 1997. Presence of foetal DNA in maternal plasma and serum. Lacet 350: 485-487.
56. Lo Y M, Chan K C, Sun H, Chen E Z, Jiang P, Lun F M, Zheng Y W, Leung T Y, Lau T K, Cantor C R, Chiu R W. 2010. Maternal plasma DNA sequencing reveals the genome-wide genetic and mutational profile of the fetus. Science Transl Med 2: 61
57. Loh Y H, Agarwal S, Park I H, Urbach A, Huo H, Heffner G C, Kim K, Miller J D, Ng K, Daley G Q. 2009. Generation of induced pluripotent stem cells from human blood. Blood 113: 5476-5479.
58. Lugus J J, Park C, Ma Y D, Choi K. 2009. Both primitive and definitive blood cells are derived from Flk-1+ mesoderm. Blood 113: 563-566.
59. Manotaya S, Elias S, Lewis D E, Simpson J L, Bischoff F Z. 2002. Evaluation of a culture system for enrichement of CD34+ hematopoietic progenitor cells present in maternal blood. Foetal Diagn Ther 17: 90-96.
60. Maximow A A. 1909. Untersuchungen uber blut und bindegewebe 1. Die fruhesten entwicklungsstadien der blut-und binde-gewebszellan bein saugetierembryo, bis zum anfang der blutbilding unden leber. Arch Mikroskop Anat. 73:444-561.
61. McGrath K E, Kingsley P D, Koniski A D, Porter R L, Bushnell T P, Palis J. 2008. Enucleation of primitive erythroid cells generates a transient population of "pyrenocytes" in the mammalian fetus. Blood 111: 2409-2417.
62. Muller F, Benattar C, Audibert F, Roussel N, Dreux S, Cuckle H.2003. First-trimester screening for Down syndrome in France combining foetal nuchal translucency measurement and biochemical markers. Prenat Diagn 23: 833-836.
63. Okita K, Hong H, Takahashi K, Yamanaka S. 2010. Generation of mouse-induced pluripotent stem cells with plasmid vectors. Nature Protocols 5: 418-428.
64. Palis J, Malik J, McGrath K E, Kingsley P D. 2010. Primitive erythropoiesis in the mammalian embryo. Int. Jour. Dev. Biol 54: 1011-1018.
65. Pereda J, Niimi G. 2008. Embryonic erythropoiesis in human yolk sac: two different compartments for two different processes. Microsc. Res. Tech 71: 856-862.
66. Poon L L, Leung T N, Lau T K, Lo Y M. 2000. Presence of foetal RNA in maternal plasma. Clin Chem 46: 1832-1834.
67. Popova E Y, Krauss S W, Short S A, Lee G, Villalobos J, Etzell J, Koury M J, Ney P A, Chasis J A, Grigoryev S A. 2009. Chromatin condensation in terminally differentiating mouse erythroblasts does not involve special architectural proteins but depends on histone deacetylation. Chromosome Res. 17: 47-64.
68. Price J O, Elias S, Wachtel S S, Klinger K, Dockter M, Tharapel A, Shulman L P, Phillips O P, Meyers C M, Shook D, Simpson J L. 1991. Prenatal diagnosis with foetal cells isolated from maternal blood by multiparameter flow cytometry. Am J Obstet Gynecol 165: 1731-1737.
69. Prieto B, Alonso R, Paz A, Cándenas M, Venta R, Ladenson J H, Alvarez F V. 2001. Optimization of nucleated red blood cells (NRBC) recovery from maternal blood collected using both layers of a double density gradient. Prenat Diagn 21: 187-193.
70. Saito H, Sekizawa A, Morimoto T, Suzuki M, Yanaihara T. 2000. Prenatal DNA diagnosis of a single-gene disorder from maternal plasma. Lancet 356: 1170.
71. Samura O, Sekizawa A, Zhen D K, Falco V M, Bianchi D W. 2000. Comparison of foetal cell recovery from maternal blood using a high density gradient for the initial separation step: 1.090 versus 1.119 g/ml. Prenat Diagn 20: 281-286.
72. Sangiorgi F, Woods C M, Lazarides E. 1990. Vimentin downregulation is an inherent feature of murine erythropoiesis and occurs independently of lineage. Development 110: 85-96.
73. Sasaki K, Kendall M D. 1985. The morphology of the haemopoietic cells of the yolk sac in mice with particular reference to nucleolar changes. J. Anat. 140: 279-295.
74. Schmorl C G. 1893. Pathologisch-Antomische Untersuchungen uber Puerperal Eklampsie. [Pathological-anatomical explorations on puerperal eclampsia]. Leipzig, Germany: Verlag FCW Vogel.
75. Schroder J, De la Chapelle A. 1972. Foetal lymphocytes in the maternal blood. Blood 39: 153-162.
76. Staerk J, Dawlaty M M, Gao Q, Maetzel D, Hanna J, Sommer C A, Mostoslaysky G, Jaenisch R. 2010. Reprogramming of human peripheral blood cells to induced pluripotent stem cells. Cell stem cell 7: 20-24.
77. Steele M W, Breg W R. 1966. Chromosome analysis of human amniotic-fluid cells. The Lancet 287: 383-385.
78. Takahashi K, Tanabe K, Ohnuki M, Narita M, Ichisaka T, Tomoda K, Yamanaka S. 2007. Induction of pluripotent stem cells from adult human fibroblasts by defined factors. Cell 131: 861-872.
79. Tabor A, Vestergaard C H, Lidegaard Ø. 2009. Foetal loss rate after chorionic villus sampling and amniocentesis: an 11-year national registry study. Ultrasound Obstet Gynecol. 34: 19-24.
80. Troeger C, Holzgreve W, Hahn S. 1999. A comparison of different density gradients and antibodies for enrichment of foetal erythroblasts by MACS. Prenat Diagn 19: 521-526.

81. Tutschek B, Reinhard J, Kögler G, Wernet P, Niederacher D. 2000. Clonal culture of foetal cells from maternal blood. Lancet 356: 1736-1737.
82. Valerio D, Aiello R, Altieri V, Malato A P, Fortunato A, Canazio A. 1996. Culture of foetal erythroid progenitor cells from maternal blood for non-invasive prenatal genetic diagnosis. Prenat Diagn 16: 1073-1082.
83. Valerio D, Altieri V, Antonucci F R, Aiello R. 1997. Characterization of foetal hematopoietic progenitors circulating in maternal blood of seven aneuplid pregnancies. Prenat Diagn 17: 1159-1169.
84. Valerio D, Altieri V, Cavallo D, Aiello R, Antonucci F R. 2000. Detection of foetal trisomy 18 by short-term culture of maternal peripheral blood. Am J Obstet Gynecol 183: 222-225.
85. Van Handel B, Prashad S L, Hassanzadeh-Kiabi N, Huang A, Magnusson M, Atanassova B, Chen A, Hamalainen E I, Mikkola H K. 2010. The first trimester placenta is a site for terminal maturation of primitive erythroid cells. Blood 116: 3321-3330.
86. Voullaire L, loannou P, Nouri S, Williamson R. 2001. Foetal nucleated red blood cells from CVS washings: an aid to development of first trimester non-invasive prenatal diagnosis. Prenat Diagn 21: 827-834.
87. Vrettou C, Traeger-Synodinos J, Tzetis M, Malamis G, Kanavakis E. 2003. Rapid screening of multiple beta-globin gene mutations by real-time PCR on the Light Cycler: application to carrier screening and prenatal diagonsis of thalassemia syndromes. Clin Chem 49: 769-776.
88. Walknowska J, Conte F A, Grumbach M M. 1969. Practical and theoretical implications of foetal-maternal lymphocyte transfer. Lancet 1: 1119-1122.
89. Weise M, Gabriel D, Tanner B. 1984. Growth behavior of amnion cell cultures. Zentralbl Allg Pathol 129: 499-505.
90. Woltjen K, Michael I P, Mohseni P, Desai R, Mileikovsky M, Hämäläinen R, Cowling R, Wang W, Liu P, Gertsenstein M, Kaji K, Sung H K, Nagy A. 2009. piggyBac transposition reprograms fibroblasts to induced pluripotent stem cells. Nature 458: 766-770.
91. Yakobov E, Rechavi G, Rozenblatt S, Givol D. 2010. Reprogramming of human fibroblasts to pluripotent stem cells using mRNA of four transcription factors. Biochem Biophys Res Commun 394: 189-193.
92. Ye L, Chang J C, Lin C, Sun X, Yu J, Kan Y W. 2010. Induced pluripotent stem cells offer new approach to therapy in thalassemia and sickle cell anemia and option in prenatal diagnosis in genetic diseases. Proc Natl Acad Sci USA 106: 9826-9830.
93. Yoshida H, Kawane K, Koike M, Mori Y, Uchiyama Y, Nagata S. 2005. Phosphatidylserine-dependent engulfment by macrophages of nuclei from erythroid precursor cells. Nature 437: 754-758.
94. Yu J, Vodyanik M A, Smuga-Otto K, Antosiewicz-Bourget J, Frane J L, Tian S, Nie J, Jonsdottir G A, Ruotti V, Stewart R, Slukvin I I, Thomson J A. 2007. Induced pluripotent stem cell lines derived from human somatic cells. Science 318: 1917-1920.
95. Zimmermann B, Holzgreve W, Zhong X Y, Hahn S. 2002. Inability to clonally expand foetal progenitors from maternal blood. Foetal Diagn Ther 17: 97-100.
96. Zhou H, Wu S, Joo J Y, Zhu S, Han D W, Lin T, Trauger S, Bien G, Yao S, Zhu Y, Siuzdak G, Schöler H R, Duan L, Ding S. 2009. Generation of induced pluripotent stem cells using recombinant proteins. Cell stem cell 4: 381-384.
97. Zhu S, Li W, Zhou H, Wei W, Ambasudhan R, Lin T, Kim J, Zhang K, Ding S. 2010. Reprogramming of human primary somatic cells by OCT4 and chemical compounds. Cell stem cell 7: 651-655.

The invention claimed is:

1. A method of identifying and isolating at least one primitive foetal erythroblast from a first trimester sample, the method consisting of:
 (a) a method for identifying one or more primitive foetal erythroblasts in cells of the first trimester sample, said method for identifying consisting of:
  (1) staining at least one nucleated CD45 negative cell in the sample with a nuclear stain to obtain one or more nuclear stained CD45 negative cells and therefrom determining presence in the sample of at least one CD45 negative cell having a cytoplasmic-to-nuclear ratio of 16:1 to 9:1; and
  (2) selecting said at least one CD45 negative cell having a cytoplasmic-to-nuclear ratio of 16:1 to 9:1 and further having:
   (i) a cell diameter within a range of 10-20 μm, and
   (ii) a smooth non-sticking cell surface,
  and therefrom identifying one or more primitive foetal erythroblasts in cells of the first trimester sample; and
 (b) isolating one or more of said primitive foetal erythroblasts identified in (a) by picking the one or more primitive foetal erythroblast from the sample with at least one micromanipulator to obtain an isolated primitive foetal erythroblast,
wherein the isolated primitive foetal erythroblast is capable of being cultured.

2. The method according to claim 1, wherein the primitive foetal erythroblast is of mammalian origin.

3. The method according to claim 1, wherein the primitive foetal erythroblast is of human origin.

4. A method of identifying and isolating at least one primitive foetal erythroblast from a first trimester sample, the method comprising:
 (a) a method for identifying one or more primitive foetal erythroblasts in cells of the first trimester sample, said method for identifying consisting of:
  (1) staining at least one nucleated CD45 negative cell in the sample with a nuclear stain to obtain one or more nuclear stained CD45 negative cells and therefrom determining presence in the sample of at least one CD45 negative cell having a cytoplasmic-to-nuclear ratio of 16:1 to 9:1; and
  (2) selecting said at least one CD45 negative cell having a cytoplasmic-to-nuclear ratio of 16:1 to 9:1 and further having:
   (i) a cell diameter within a range of 10-20 μm,
   (ii) a smooth non-sticking cell surface,
  and therefrom identifying one or more primitive foetal erythroblasts in cells of the first trimester sample;
 (b) isolating one or more of said primitive foetal erythroblasts identified in (a) by picking the one or more primitive foetal erythroblast from the sample with at least one micromanipulator to obtain an isolated primitive foetal erythroblast, wherein the isolated primitive foetal erythroblast is capable of being cultured; and
 (c) culturing the isolated primitive foetal erythroblast in a medium comprising at least one mitogen or at least one epigenetic factor, or at least one mitogen and at least one epigenetic factor, wherein the mitogen is selected from the group consisting of concanavalin A, phytohaemagglutinin, lipopolysaccharide (LPS), Insulin-like growth factors (IGFs) and pokeweed mitogen, and wherein the epigenetic factor is selected from (i) at least one histone deacetylase inhibitor or at least one DNA methyl transferase inhibitor, or (ii) at least one histone deacetylase inhibitor and at least one DNA methyl transferase inhibitor.

5. The method according to claim 4, wherein the medium is free from at least one growth factor.

6. The method according to claim 4, wherein the method is carried out under normoxic conditions.

7. The method according to claim 4, wherein the primitive foetal erythroblast is maintained in a microdroplet.

8. The method according to claim 7, wherein the microdroplet is overlaid with at least one mineral oil.

9. The method according to claim 4, wherein the medium is capable of increasing viability of the primitive foetal erythroblast.

10. The method according to claim 4, wherein the medium is capable of maintaining cell viability of the primitive foetal erythroblast for at least 48 hours.

* * * * *